(12) United States Patent
Weiss

(10) Patent No.: US 6,466,819 B1
(45) Date of Patent: Oct. 15, 2002

(54) CARDIOELECTRIC APPARATUS

(75) Inventor: Ingo Weiss, Erlangen (DE)

(73) Assignee: Biotronik Mess-und Therapiegerate GmbH & Co. Ingenieurburo Berlin, Berlin (DE)

(*) Notice: Subject to any disclaimer, the term of this patent is extended or adjusted under 35 U.S.C. 154(b) by 0 days.

(21) Appl. No.: 09/603,076

(22) Filed: Jun. 26, 2000

Related U.S. Application Data

(63) Continuation of application No. 09/603,076, filed on Jun. 26, 2000.

(30) Foreign Application Priority Data

Jun. 25, 1999 (DE) .......................................... 199 30 270

(51) Int. Cl.⁷ .......................... A61N 1/39; A61B 5/0464
(52) U.S. Cl. ............................................ 607/5; 600/518
(58) Field of Search .................................. 600/508, 509, 600/518, 515, 516; 607/4, 5, 9, 14, 25

(56) References Cited

U.S. PATENT DOCUMENTS

| | | | | |
|---|---|---|---|---|
| 5,437,285 A | * | 8/1995 | Verrier et al. ................ | 600/515 |
| 5,560,368 A | * | 10/1996 | Berger ......................... | 600/517 |
| 5,709,214 A | * | 1/1998 | Skinner ....................... | 600/515 |
| 5,978,700 A | * | 11/1999 | Nigam ......................... | 600/518 |

FOREIGN PATENT DOCUMENTS

| | | |
|---|---|---|
| DE | 196 09 365 | 9/1997 |
| DE | 198 30 316 | 2/1999 |

OTHER PUBLICATIONS

German Search Report DE 199 30 270.7.
Benda, D., "Elektronische Patientenuberwachung", In: Elektronik, 1971, H. 11, pp.389–394: Kapitel 3.1.3.

Badilini, F., et al., "QT interval analysis on ambulatory electrocardiogram recordings: a selective beat averaging approach", In: Medical & Biological Engineering & Computing, 1999, vol. 37, pp. 71–79.
Beeler, G.W., et al., "Reconstruction of the Action Potential of Ventricular Myocardial Fibers", J. Physiol. 1977, 268, pp. 177–211.
Franz, M. et al., "Electrical Remodeling of the Human Atrium: Similar Effects in Patients With Chronic Atrial Fibrillation and Atrial Flutter", JACC, Dec. 1997, pp. 1785–1791, vol. 30, No. 7.

(List continued on next page.)

Primary Examiner—George R. Evanisko
(74) Attorney, Agent, or Firm—Christie, Parker & Hale, LLP

(57) ABSTRACT

A cardioelectric apparatus for the early detection of a tachycardia of the heart is provided. The cardioelectric apparatus of the current invention, comprising: 1) measurement means for sensing measurement values for the heart rate and the action potential duration, the measurement means having at least one output for the output of measurement value pairs of mutually associated measurement values for the heart rate and the action potential duration; 2) measurement value processing means for receiving the measurement value pairs, the measurement value processing means connected to the output of the measurement means and which are adapted to derive from the measurement value pairs time-variant parameters ($\tau_x$, g) which describe the heart; 3) a memory in which comparative values characterizing a tachycardia risk can be stored; and 4) an evaluation unit connected to the measurement value processing means for receiving the parameters ($\tau_x$, g) derived from the measurement value pairs and further connected to the memory and which is adapted to compare the derived parameters ($\tau_x$, g) to comparative values stored in the memory and to output a tachycardia risk signal if the comparison of the derived parameters ($\tau_x$, g) with the comparative values shows that the derived parameters ($\tau_x$, g) are in the tachycardia risk range.

7 Claims, 17 Drawing Sheets

OTHER PUBLICATIONS

Hnatkova, K., et al., "Analysis of the cardiac rhythm preceding episodes of paroxysmal atrial fibrillation", American Heart Journal, 1998, pp. 1010–1019, vol. 35, No. 6, Part 1.

Horer, S.M., et al., "Cycle Length Dependence of the Electrophysiological Effects of Increased Load on the Myocardium", Circulation, Sep. 1996, pp. 1131–1136, vol. 94, No. 5.

Horer, S.M., et al., "Sympathomimetic modulation of load–dependent changes in the action potential duration in the situ porcine heart", Cardiovascular Research 32,Jul. 1996,pp. 148–157.

Qi, A., et al., "Characteristics of restitution kinetics in repolarization of rabbit atrium", Can. J. Physiol. Pharmacol. vol. 75, pp. 255–262, Apr. 1997.

Taggart, P. et al., "Human Ventricular Action Potential Action Potential Duration During Short and Long Cycles: Rapid Modulation by Ischemia", Circulation, pp. 2526–2534, vol. 94, No. 10, Nov. 1996.

Verduyn, S.C., "Further Oberservations to Elucidate the Role of Intraventricular Dispersion of Refractoriness and Early Afterdepolarizations in the Genesis of Acquired Torsade de Pointes Arrhythmias", JACC, pp. 1575–1584, Nov. 1997, vol. 30, No. 6.

Volders, et al., "Cellular Basis of Biventricular Hypotrophy and Arrhythmogenesis in Dogs With Chronic Complete Atrioventicular Block and Acquired Torsade de Pointes", Circulation, Sep. 1998, pp. 1136–1147, vol. 98.

Weiss, I., et al., "New Aspects of Arrhythmogenesis Investigated in a Model of EAD–Induced Cardiac Reentry", $19^{th}$ Annual International Conference of the IEEE EMBS, 1997 (Abstract).

Weiss, I., et al., "A Model Study of Cardiac Early Afterdepolarizaitons", Progress in Biomedical Research, Dec. 1996, pp. 84–93.

Zeng, J., et al., "Early Afterdepolarizations in Cardiac Myocytes: Mechanism and Rate Dependence", Biophysical Journal 1995, vol. 68, pp. 949–964.

* cited by examiner

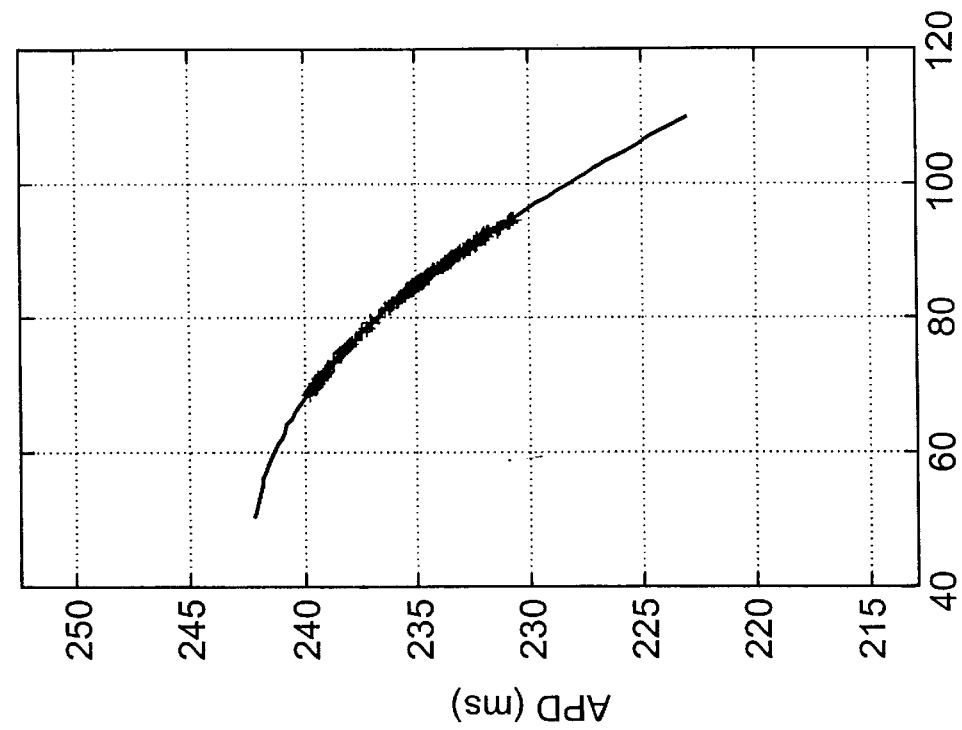
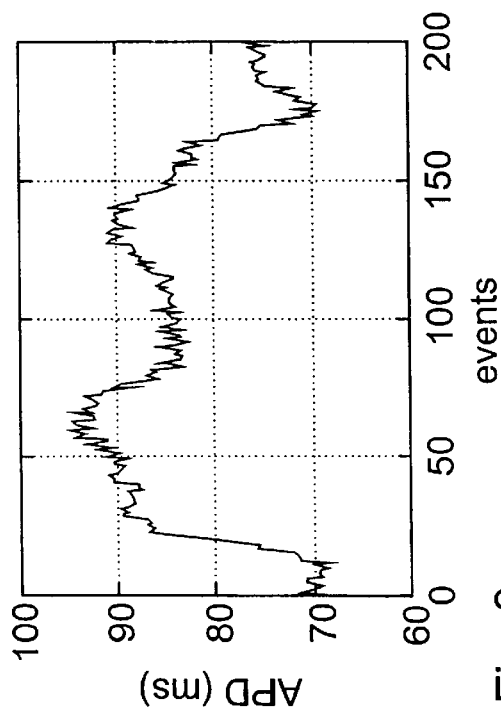
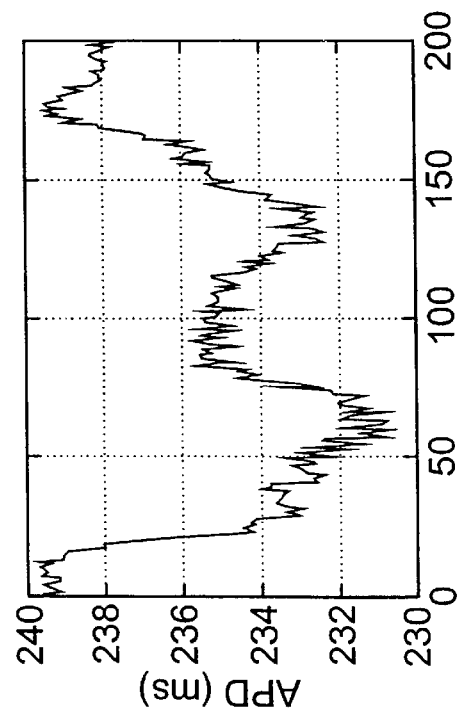
Fig. 9a
Fig. 9b
Fig. 9c

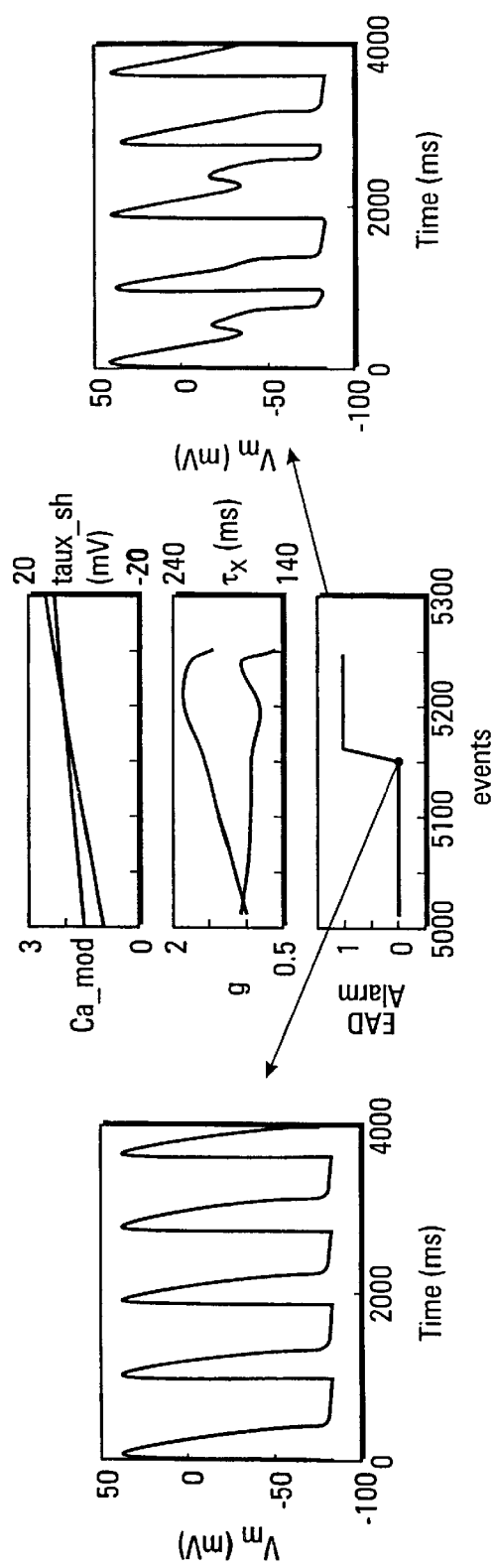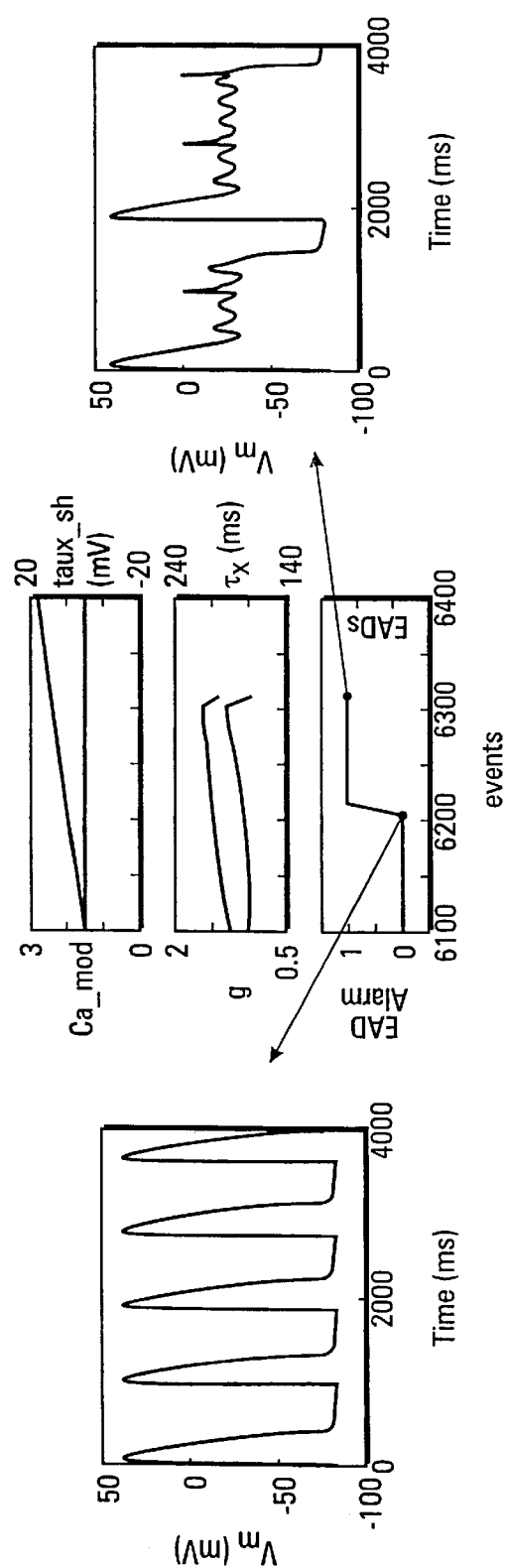
Fig. 17a
Fig. 17b

CARDIOELECTRIC APPARATUS

CROSS-REFERENCE TO RELATED APPLICATION

This application is a continuation of U.S. application Ser. No. 09/603,076, filed Jun. 26, 2000, which claims priority on German Patent Application No. 199.30.270.7, filed Jun. 25, 1999.

FIELD OF THE INVENTION

The invention concerns an apparatus for early detection of a tachycardia of a heart.

BACKGROUND OF THE INVENTION

The human heart, can go into physiologically disturbing and possibly fatal states. One such state is a tachycardia, which is distinguished by very rapidly succeeding heart beats, that is to say a high heart rate with a simultaneously reduced pumping capacity on the part of the heart.

Apparatuses for detecting and treating such tachycardia phenomena, for example cardioverters or defibrillators, are well-known. A disadvantage of the known apparatuses are that they detect a tachycardia situation only when it has already occurred.

Accordingly, a need exists for an apparatus which is capable of detecting a tachycardia before the event occurs, that is to say before the beginning of the tachycardia.

SUMMARY OF THE INVENTION

The present invention is directed to a cardioelectric apparatus for early detection of a tachycardia of a heart. The cardioelectric apparatus of the current invention includes the following components:

a) measurement means for sensing the heart rate and the action potential duration, the measurement means having at least one output for the output of measurement value pairs of mutually associated measurement values for the heart rate and action potential duration;

b) measurement value processing means connected to the output of the measurement means for receiving the measurement value pairs, the measurement value processing means adapted to derive from the measurement value pairs time-variant parameters which describe the heart;

c) a memory in which comparative values characterizing a tachycardia risk are stored; and d) an evaluation unit connected to the memory and the measurement value processing means for receiving the parameters derived from the measurement value pairs, the evaluation unit being adapted to compare the derived parameters to comparative values stored in the memory and to output a tachycardia risk signal if the comparison of the derived parameters with the comparative values shows that the derived parameters are within the tachycardia risk range.

In such an embodiment, the cardioelectric apparatus of the invention is capable of detecting a threatening tachycardia before it occurs. Any method of deriving from the measurement pair values time-variant parameters which describe the heart may be utilized in the current invention, but one method is described in detail hereinafter. Likewise, any conventional method of deriving the heart rate, that is to say the pulse rate of the heart, and the action potential duration, may be utilized. In addition, any conventional design of the apparatus such that it is in a position to establish whether certain parameters fall into a certain parameter range may be utilized in the current invention.

In an alternative embodiment, the cardioelectric apparatus of the current invention is adapted to sense at least two measurement value pairs at different measurement times. In such an embodiment, the cardioelectric apparatus additionally comprises a second storage means or memory connected to the measurement value processing means, the memory being capable of storing at least the parameters derived for the two latest measurement times, the cardioelectric apparatus further comprising trend-determining means connected to the second memory adapted to determine a trend for the future development of the parameters on the basis of the stored parameters, wherein the evaluation unit is connected to the trend-determining means and is so designed to output the tachycardia risk signal when the derived parameters are in the proximity of the tachycardia risk range and the trend for future development of the parameters points in the direction of the tachycardia risk range. In such an embodiment, the cardioelectric apparatus according to the invention is capable of detecting a tachycardia risk before the ascertained parameters fall into a dangerous range, by determining when the parameters derived from the measurement value pairs are trending toward the risk range.

In another alternative embodiment of the present invention, the cardioelectric apparatus is adapted to sense at least two measurement value pairs at different measurement times and additionally has a second storage means or memory which is connected to the measurement value processing means to store at least the parameters derived for the two respective latest measurement times. The cardioelectric apparatus further comprises trend-determining means connected to the second memory and adapted to extrapolate future parameters from the stored parameters, wherein the evaluation unit is connected to the trend-determining means and is adapted to compare the extrapolated parameters to comparative values stored in the memory and to output a tachycardia risk signal if the comparison of the extrapolated parameters with the comparative values shows that the extrapolated parameters are in the tachycardia risk range.

In yet another alternative embodiment of the present invention, the derived parameters describe time-variable bidirectional ion currents between the cell interior and the cell exterior of heart muscle cells, which include a static and a dynamic potassium ion current and a calcium ion current. In such an embodiment, the first of the parameters ($\tau_x$) is a time constant of the dynamic potassium ion current, and the second of the parameters (g) is a difference ($A_{Ca}-A_{Kl}$), related to the amplitude of the dynamic potassium ion current ($A_{Kx}$), of the amplitudes of the calcium ion current ($A_{Ca}$) and the static potassium ion current ($A_{Kl}$) according to the equation:

$$g=((A_{Ca}-A_{Kl})/A_{Kx}) \qquad (1)$$

In still another alternative embodiment of the present invention, the first parameter ($\tau_x$) represents the time constant of the dynamic potassium channel of the heart muscle cells, and the second parameter (g) represents the ratios $((A_{Ca}-A_{Kl})/(A_{Kx}))$ between the permeabilities of the calcium channel ($A_{Ca}$), the static potassium channel ($A_{Kl}$), and the dynamic potassium channel ($A_{Kx}$) of the heart muscle cells.

In still yet another alternative embodiment of the present invention, the cardioelectric apparatus comprises an electrostimulator, such as a cardioverter, or a defibrillator, wherein the electrostimulator is connected to the evaluation unit for receiving the tachycardia risk signal and is adapted to be triggered by the tachycardia risk signal to output tachycardia-combating electrical stimulation pulses to the heart.

BRIEF DESCRIPTION OF THE DRAWINGS

The above and other aspects, features and advantages of the present invention will be more apparent from the following more particular description thereof, presented in conjunction with the following drawings wherein:

FIG. 9a is a graphical depiction of a parameter estimation algorithm according to the present invention;

FIG. 9b is a graphical depiction of a parameter estimation algorithm according to the present invention;

FIG. 9c is a graphical depiction of a parameter estimation algorithm according to the present invention;

FIG. 17a is a graphical depiction of a detailed predictor simulation for EAD-governed tachycardia according to the present invention; and FIG. 17b is a graphical depiction of a detailed predictor simulation for EAD-governed tachycardia according to the present invention.

DETAILED DESCRIPTION OF THE INVENTION

The present invention is directed to a cardioelectric apparatus for early detection of a tachycardia of a heart.

Figure 1:
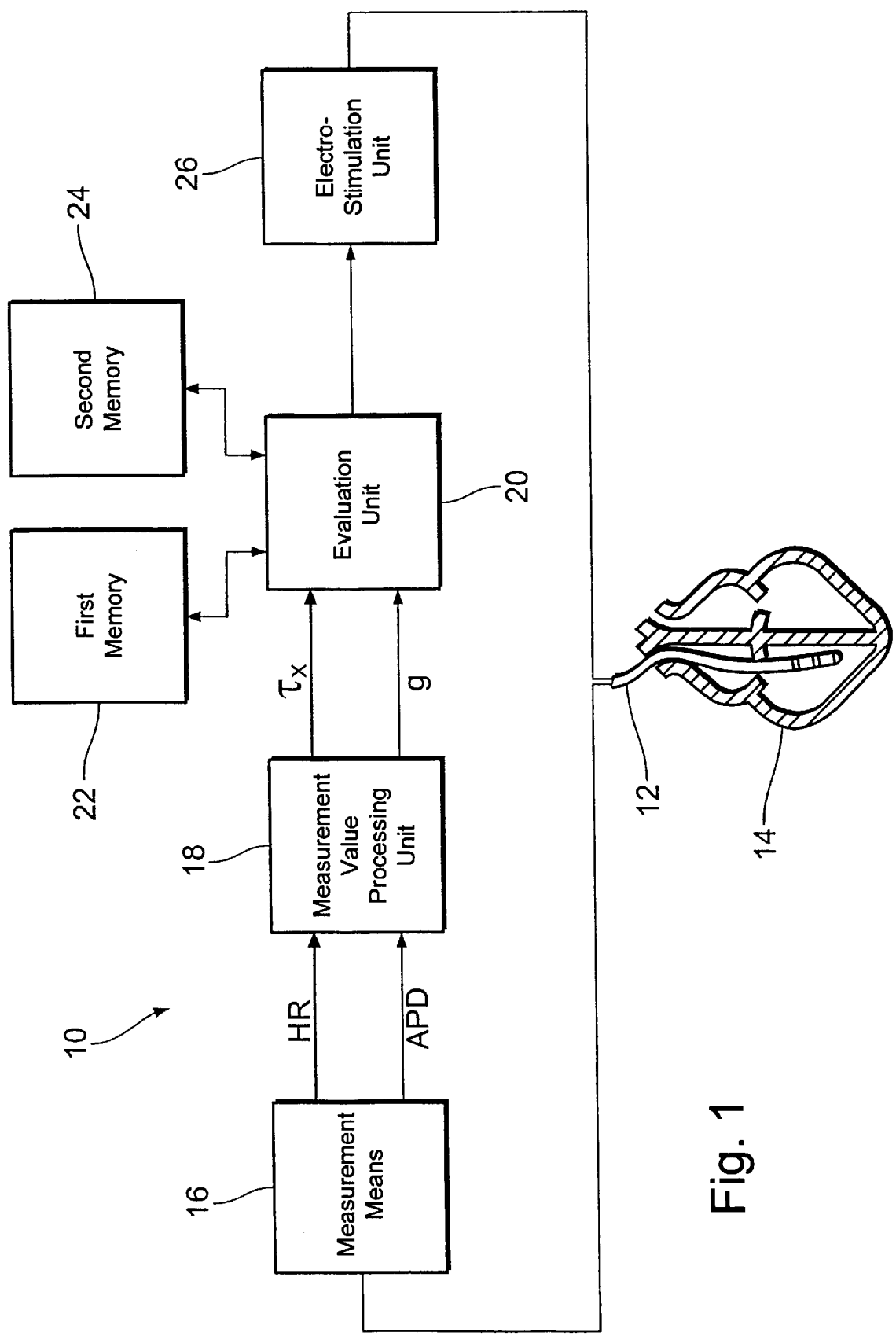
FIG. 1 is a schematic of a cardioelectric apparatus for the early detection of a tachycardia of a heart according to the present invention.

Referring to FIG. 1, the cardioelectric apparatus 10 according to the present invention includes an electrode line 12 connected to a measurement unit 16 for sensing electrical signals of a heart 14. The measurement unit or measurement means 16 derive from the sensed electrical signals measurement values for the heart rate (HR) or the reciprocal of the heart rate HR, the cycle length (L); or the depolarization time (T), and the action potential duration (APD) of the heart. These measurement value pairs are ascertained at various moments in time and transmitted to a measurement value processing unit 18, which is connected at the input side to corresponding outputs of the measurement unit 16.

The measurement value processing unit 18 derives the time constant ($\tau_x$) of the dynamic potassium channel of the heart muscle cells of the heart 14 and a difference (g) of the calcium current amplitude ($A_{Ca}$) and the potassium current amplitude ($A_{K1}$), related to the amplitude of the dynamic potassium current $A_{Kx}$, from the depolarization time T or the action potential duration APD; and the heart rate HR or its reciprocal, the cycle length L. Accordingly, the difference g represents the ratios of the levels of permeability of the calcium and potassium channels.

Derivation of the parameters g and $\tau_x$ are based on the model described hereinafter of a heart as a time-variable system in which $\tau_x$ and g are time-variant structural parameters. The operation of deriving those parameters is effected by the described linearization procedure, wherein the basic starting point adopted is a selected linearization point within the model and iterative approximation to the actual working point of the heart. The details of this derivation procedure are described more fully hereinafter.

The derived parameters $\tau_x$ and g are transmitted by the measurement value processing unit 18 in the form of mutually associated value pairs to an evaluation unit 20, which is connected on the input side to the output of the measurement value processing unit 18. In addition, the evaluation unit 20 is connected to a first storage means or memory 22 and a second storage means or memory 24 which can form a physical unit. The first memory 22 stores comparative values for the parameters $\tau_x$ and g which characterize a danger zone or a tachycardia risk range, that is to say comparative values for such pairs of values of the parameters $\tau_x$ and g which indicate risk of tachycardia. In this respect, the evaluation unit 20 is such that it compares the derived values for the parameters $\tau_x$ and g, as received from the measurement value processing unit 18, to the comparative values stored in the first memory 22, and outputs a tachycardia risk signal if the comparison should show that the values for the parameters $\tau_x$ and g, which are ascertained by the measurement value processing unit 18, fall within the danger zone, i.e., the tachycardia risk range.

The second memory 24 stores pairs of values for values of the parameters $\tau_x$ and g, which were derived at earlier measurement times. By means of comparison of the most recently derived values for the parameters $\tau_x$ and g to those of preceding measurement times, the evaluation unit 20 can determine a trend with respect to future values of the parameters $\tau_x$ and g. If that trend points in the direction of such values of $\tau_x$ and g which lie in the danger zone or the tachycardia risk range, the evaluation unit 20 then outputs a tachycardia risk signal if the values of the parameters last delivered by the measurement value processing unit 18 are not in the danger zone. Alternatively, the evaluation unit 20 may extrapolate future values of $\tau_x$ and g from the values of $\tau_x$ and g last delivered by the measurement value processing unit 18 and the values of preceding measurement times which were stored in the second memory 24. In such a case, if the extrapolated parameter values are in the tachycardia risk range, the evaluation unit 20 will also outputs a tachycardia risk signal.

The tachycardia risk signal is transmitted to an electrostimulation unit 26 connected to the evaluation unit 20. The electrostimulation unit 26 can be an electrostimulator, such as, for example, a cardioverter or a defibrillator. The electrostimulation unit 26 is connected by way of an electrical line to electrically conducting surface regions of the electrode line 12 introduced into the heart 14 to output stimulation pulses to the heart 14 in a conventional manner to combat a tachycardia situation.

In this respect the electrode line 12 can be connected in any conventional manner to the apparatus 10 so that the lines leading to the conducting surface regions, which can be in the form of a ring or tip electrode, can be switched over such that the electrically conducting surface regions can be utilized both for outputting stimulation pulses to the heart 14 and for receiving electrical signals from the heart 14. In the receiving switching state, the electrically conducting surface regions are connected to the measurement unit 16 in order to feed electrical signals of the heart thereto. In the stimulation switching state, the electrically conducting surface regions are connected to the electrostimulation unit 26 in order to output electrical stimulation pulses to the heart 14.

To better illustrate the invention, the following description sets forth the following: 1) a derivation of the parameters $\tau_x$ and g from measurement values of the heart rate and the action potential duration; 2) a description of the procedure for recognizing a trend in these parameters; and 3) information relating to the tachycardia risk range which is referred to hereinafter as the danger zone.

Heart System Description

When looking for early symptoms of an incipient arrhythmia essentially two aspects crystallize out, which concern the co-ordination of the time of myocardium excitation and the readiness of the substrate for an arrhythmia situation.

Of the possible options already outlined above for the early detection of cardiac disrhythmia phenomena, this description details the question of whether and how conclusions can be drawn with respect to an electrophysiological change in the heart muscle tissue from system observation. It is known that randomly occurring, so-called ectopic heart beats are to be observed even in a healthy person. However, clinical studies show that, in corresponding heart ailments, even just a single stimulus which occurs in a critical time window can trigger off arrhythmia. The reason the ectopic heart beat does not trigger an arrhythmia in the healthy myocardium is to be attributed to the different functional properties of the healthy and the diseased syncytium.

A further consideration in terms of identifying early symptoms of an incipient arrhythmia by analysis of the substrate properties is that, on the basis of expectation, changes in the substrate are a consequence of a longer-term process. Therefore, by means of this approach the risk of arrhythmia can be detected long before the occurrence of cardiac disrhythmia phenomena and thus subjected to therapy.

The subject of the considerations involve the myocardial syncytium, which is manifested in the form of a non-linear dynamic system. The aim, based on methods of system identification, is to define and quantitatively determine parameters which characterize arrhythmia-relevant properties of the syncytium. To implement system identification, input and output signals must be known, wherein the input signal must deflect the system, that is to say stimulate the internal state values. The specific selection of input and output signals is effected by the physiological criteria, which are discussed at a later point. If the system can be observed in the system-theoretical sense, it is possible to ascertain the system parameters from the transfer behavior. In a specific case that requirement can be somewhat restricted insofar as the system must be observable (only) with respect to arrhythmia-relevant parameters.

Establishing arrhythmia-relevant parameters is dependent on the model approach for the system to be observed. In a practical context, generally in the absence of more detailed information about the system, a "black box" description is adopted, in which case it is only the order of the system that is to be established. Additionally, if the system is linear, then established processes of system identification can be referenced. As however the myocardial syncytium is a non-linear system, a description of the system under consideration must be described as a chain linkage of a linear dynamic and a non-linear static system portion. Then, by identifying the linear component, which in the literature is based on a "black box" description, it is possible to use a standard process. The disadvantage of the "black box" approach, however, is that it is not possible to associate with the parameters resulting therefrom, any immediate physiological significance. Consequently, the criteria and threshold values for arrhythmia prediction must be derived on the basis of numerous clinical studies and statistical analyses.

Figure 2:
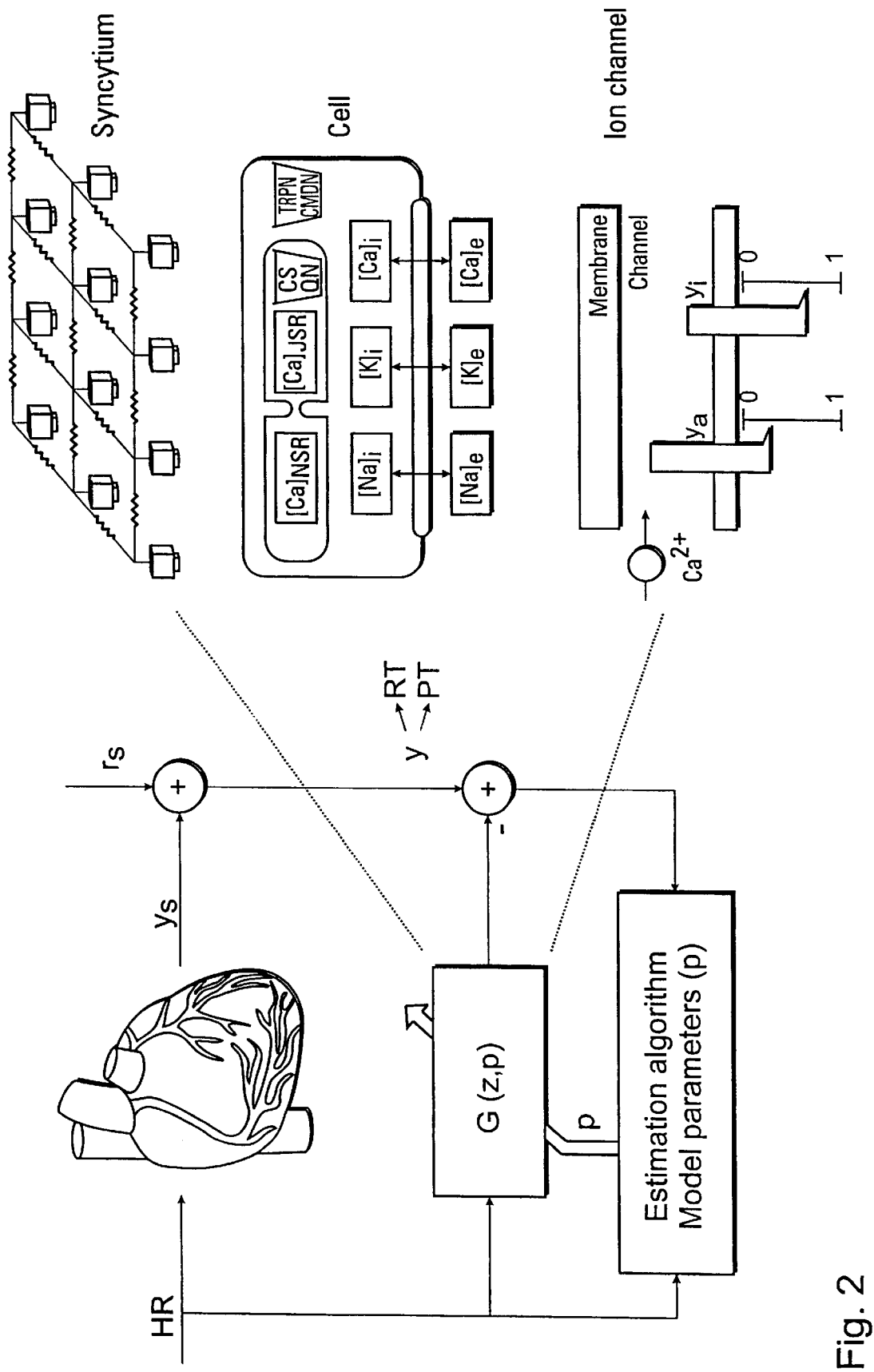
FIG. 2 is a flow-chart of a method of detecting a tachycardia of a heart according to the present invention.

Therefore approach set forth herein is built on a physiologically founded model of the substrate. In this respect, model constitution is guided such that the parameters which are arrhythmia-relevant from the physiological point of view are determined. As shown in FIG. 2, the basic starting point of the approach is based on a mathematical model of the heart muscle cell, which on the one hand is to be viewed as network of nodes in the muscle tissue; and which on the other hand, by way of the dynamically acting ion channels, permits the ion current to flow between the intra- and extra-cellular space.

The specific measurement values to be adopted as the input and output signals for system identification must also be established. Based on the literature, two fundamental dynamic dependencies of physiological values are found to be informative in terms of system identification in regard to early detection of arrhythmia phenomena, namely: 1) relationship between heart rate (HR) and repolarization time (RT); and 2) the relationship between heart rate and excitation propagation rate. The excitation time or propagation time (PT) being measured between two defined measurement points.

Examining the first point, that is to say the question of what interrelationship exists between the heart rate (or the cycle length=heart beat period) and the repolarization time, as well as the question of which physiological parameters influence that relationship in the case of pathological substrate changes. First, it should be pointed out that HR is intended more precisely to mean the local heart rate, that is to say the event rate at the measurement location (for that reason also differentiated as the event rate ER). Obviously, with an already unco-ordinated excitation propagation the term heart rate is, strictly speaking, not defined at all and ER differs according to the measurement location involved. However, as the goal of the invention is to develop a method which already signal the threatening arrhythmia risk at an early stage in the disease, that is to say at a time when the heart muscle is still functioning in a very substantially normal manner, excitation takes place in a co-ordinated fashion and ER is the same as HR, irrespective of the measurement location. For that reason, and also in order to use the normal terminology, the parameter HR will always be used hereinafter.

The repolarization time represents the time interval between the cell excitation time and the time of return to the rest membrane potential, that is to say the action potential duration (APD, being representative here of $APD_{90}$). Strictly considered however it is a parameter which characterizes the individual cell.

Accordingly the values for system identification, which are to be observed in one embodiment of the current invention are as follows: 1)HR—as the input signal; and 2) RT—as the output signal.

Determining HR (as "local heart rate") is well-known at the present time. In addition, the correlation between action potential duration and, for example, the QT-interval of the ECG is also experimentally and theoretically well-known; as are the IEGM, XAP or VER, so a number of alternatives are available for determining an approximation value of the repolarization time, using a measuring procedure. Although any suitable determination technique may be utilized in the current invention, it should be understood that the final system will be decided on the basis of practical points of view, such as, clinical implementation and computer implementation of signal processing. It is to be emphasized, however, that both the input signal and also the output signal should be measurable as necessary prerequisites for system identification, at a reasonable level of technical expenditure.

The physiological information content of the dynamic relationship between HR and RT (or APD) has been investigated on many occasions in the literature, normally with regard to early symptoms of the occurrence of cardiac disrhythmia. The question of cardiac disrhythmia was investigated both in terms of clinical and also electrophysiological aspects, and two measurement protocols have been established which characterize the relationship between HR and APD in curve form: 1) determining the $APD(HR)|_0$-curve ("restitution curve"); and determining the $APD(HR)|$-curve (in the steady state).

In determining the restitution curve, the substrate is first stimulated for a time at a constant frequency and on the basis thereof a frequency jump is effected. The restitution curve results if the repolarization time of the first heart beat after the frequency jump is plotted in relation to the corresponding (new) stimulation rate.

In determining the steady state, the repolarization time is also measured for various stimulation frequencies, but only after a "steady state" was reached. As can be seen from FIG. 3a, the system obviously has an internal limit cycle. Therefore, the mean value over a plurality of cycles is taken as the steady-state value and plotted in relation to the corresponding stimulation rate.

Figure 3B:
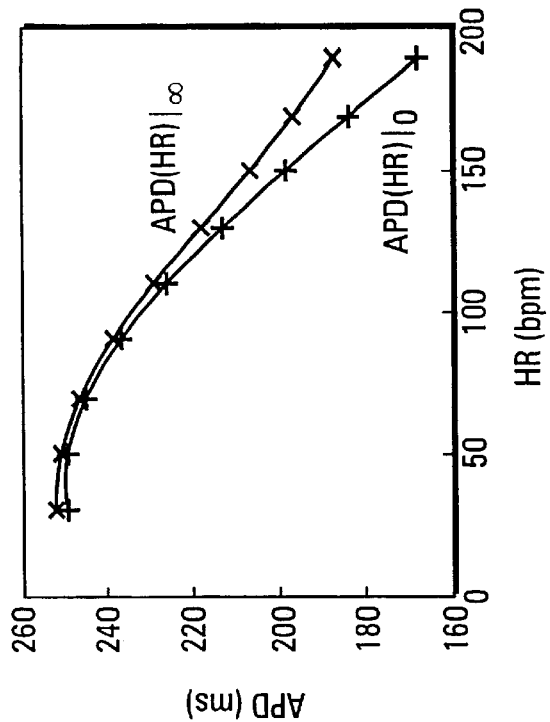
FIG. 3b is a graphical depiction of an APD measurement according to the present invention.
Figure 3A:
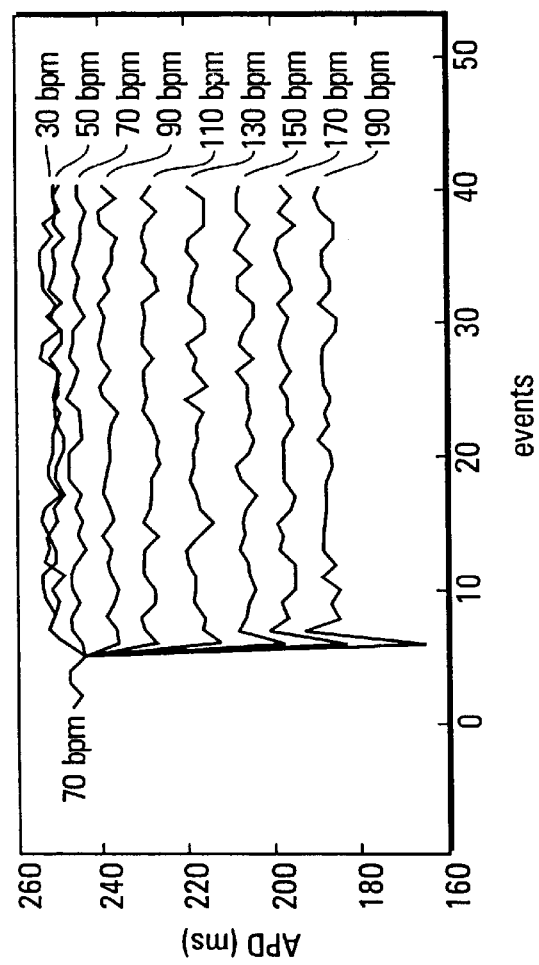
FIG. 3a is a graphical depiction of an APD measurement according to the present invention.

If we look at FIG. 3a, which shows the entire transient process as a consequence of the frequency jump, the restitution curve is obtained if the peak values are connected immediately after the jump. In contrast the $APD(HR)|$-curve results if the mean values of the APD-times are plotted at a later time.

The most important observations and conclusions in the literature in connection with determining the restitution and steady state curves and the dependency thereof on diseased or controlledly changed substrate properties can be summarized as follows:

1. Investigations with respect to the electrical remodeling phenomenon at the human atrium have shown that ahead of AF both the restitution curve and also the $APD(HR)|$-curve change and more specifically on the one hand are displaced and on the other hand become flatter.

2. In the case of ischemia-affected regions in the human endocardium, it was also possible to demonstrate a flattening of the restitution curve, in which respect conclusions with regard to arrhythmogenesis were derived therefrom. One work also refers to a general relationship between the frequency-dependent electrophysiological properties of the myocardial syncytium in the form of the restitution curve and the occurrence of cardiac disrhythmia phenomena.

3. Two further electrophysiological studies are particularly instructive in terms of establishing the arrhythmia-relevant parameters. On the one hand, based on measurements of cellular action potential the influence of sympathomimetica ($\beta$-adrenergic stimulation by the Ca-channel agonist dobutamine) was investigated and it was concluded therefrom that the observed changes in the restitution curve are related to an increase in the Ca-channel conductivity. On the other hand, it was specifically shown that changes in the restitution curve are to be attributed to properties of the K- and again the Ca-channels. In order to selectively investigate those mechanisms, specific channel blockers were used.

Based on these discoveries, it now remains to explain which physiologically justifiable model approach explains the dynamic dependency between HR and APD (or RT generally), and by way of which mechanisms certain cellular parameters influence that interrelationship. Accordingly, it is important to ascertain those parameter values by means of a systematic identification approach in order then to be able to assess the danger of arrhythmia on the basis of known electrophysiological criteria.

Based on the mathematical model description of the heart muscle cell, the relationship between repolarization time and heart rate is derived hereinafter. The aim is to describe the $APD(HR)|$-curve, which can be determined by measurement procedures, in terms of formulae, by a closed expression so that it is possible to calculate back from the measurement data to the physiological parameters which influence that interrelationship.

Figure 4:
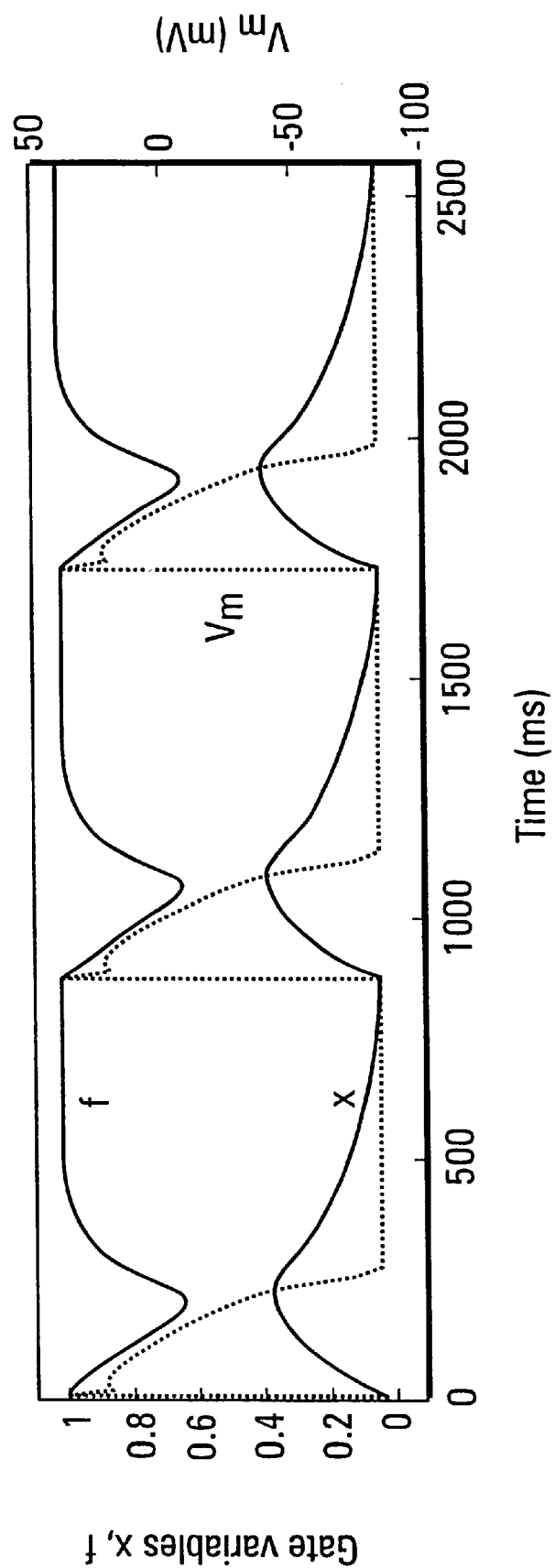
FIG. 4 is a graphical depiction of a cycle measurement according to the present invention.

Referring now to FIG. 4, tt is known both from experimental studies and also from model calculations that the action potential duration decreases if the heart rate rises or if the cycle length is reduced, and vice-versa. Clarifying the causes of that mechanism is the key question in deriving the APD(HR)-curves. If for that purpose attention is directed to the parameters of the cell model, it can be established that they change in part with very short time constants and in part with longer time constants. As a consequence, the cell embodies a stiff dynamic system. While the time constants of the fast state values are vanishingly small in comparison with the APD, the gate variables f and in particular x still do not reach their steady state, even long after return of the action potential to the rest membrane voltage. As such, the variable f describes the open state of the inactivation gate of the Ca-channel and x denotes the open state of the dynamic K-channel. Both variables vary between 0 and 1 (relative open state). With a reduced cycle length, the new stimulus occurs correspondingly earlier so that the initial values of the state variables f and x for the new cycle differ significantly from those of the previous cycle. It is therefore obvious that corresponding changes in the characteristic dimensions of the action potential are to be expected. In specific terms the initial value of x in this example is greater, that is to say the K-current already starts from an increased value. That means that the labile equilibrium of the ion currents during the plateau phase is tilted earlier in the direction of a repolarizing cell outward flow; the action potential duration is shortened.

Similar considerations can be applied to the Ca-channel. With a shortened stimulation period, the f-variable is still perceptibly less than 1, that is to say the Ca-channel is still not fully activatable. Thus, in the next cycle the Ca-current will be smaller, which on the one hand results in a reduction in the plateau height. However, on the other hand, the repolarizing K-current already predominates at an earlier time so that the consequence is also a reduction in the action potential.

Figure 5:
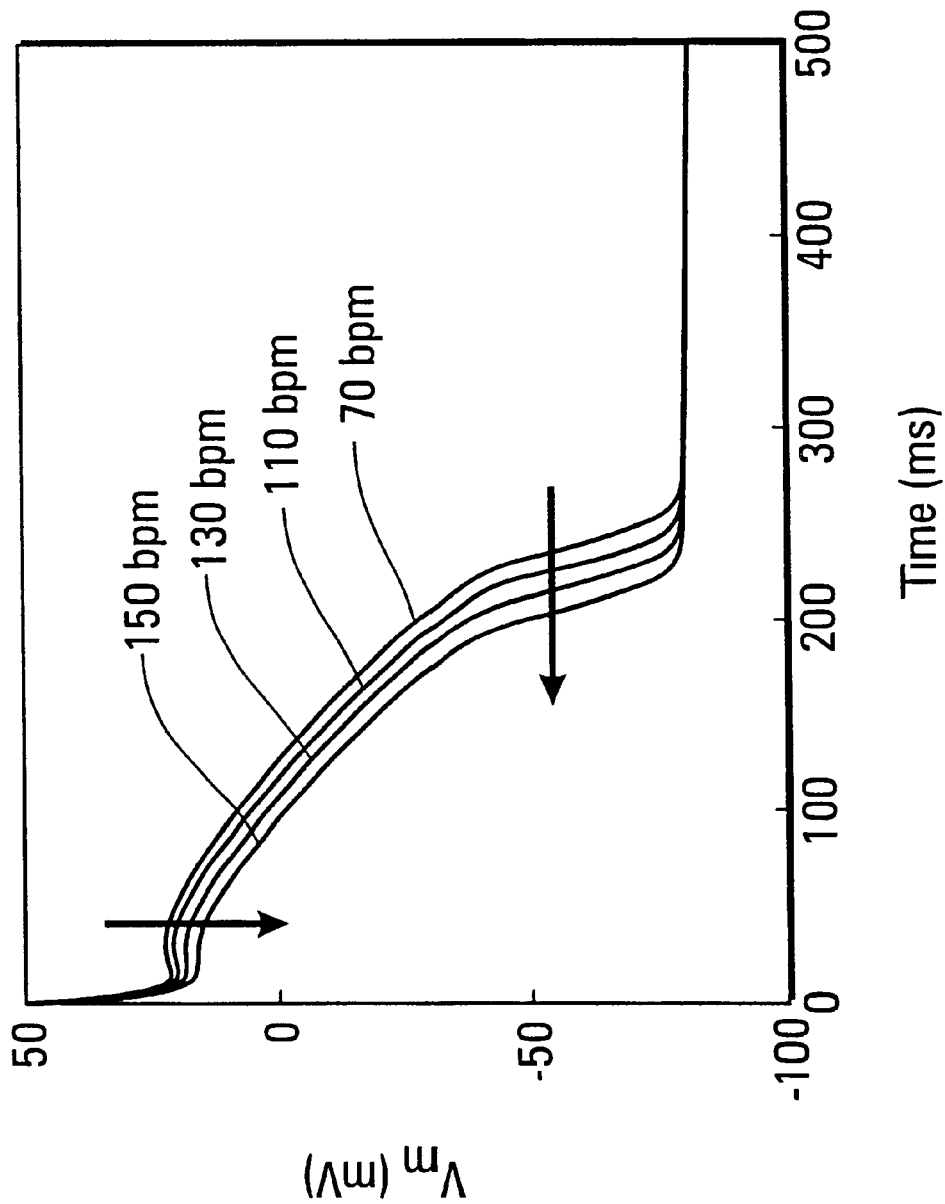
FIG. 5 is a graphical depiction of an action potential simulation according to the present invention.

FIG. 5 illustrates those effects on the basis of a simulation calculation. The dependency of the action potential duration on the stimulation rate will now be mathematically expressed. Ultimately, the problem is to arrive at an analytical expression which links these two values. However, if we consider the very extensive description and the high degree of non-linearity of the model equations, a closed analytical solution for the differential equation system is not possible. It is therefore necessary to represent the above-described phenomenon in a simplified mathematical form.

As already described in qualitative terms, the cause of the APD(HR)-dependency is to be attributed (substantially) solely to the state variables f and x, so that are also to be taken into consideration in the model approach. Accordingly, what is sought is a mathematical expression for the dynamic relationship between those state values and the repolarization time.

On the basis of the Hodgkin-Huxley-approach the dynamic behavior of such a gate variable (representatively identified by y) is described by the following initial value problem:

$$\begin{cases} \frac{dy}{dt} = \frac{y_\infty - y}{\tau_y}; t \geq t_v \\ y(t_v) = y_v \end{cases} \quad (2)$$

However, in this case it is assumed for the sake of simplification that the relaxation behavior of this variable is not dependent on the current value of the transmembrane voltage, but is characterized by a fixed time constant $\tau_y$ at an adequate level. As regards the action potential itself, a distinction is only drawn between an excited and a non-excited state so that the specific form of the action potential is a minor matter.

For these simplified model considerations the pattern of the transmembrane voltage $V_m$ is approximated by a rectangular signal whose amplitude and duration correspond to those of the action potential:

$$V_m(t) \approx V_{m0} + A_V[s(t_n) - s(t_n - T_n)] \quad (3)$$

wherein $V_{m0}$ and $A_V$ denote the rest membrane voltage and amplitude of the action potential, and s(t) is the Heaviside step function.

Accordingly, y only assumes two values, more specifically $y_s$ during the systole (excited state), and $y_d$ during the diastole (non-excited state), so that the differential Equation (2) becomes linear within each of those two time intervals. In a region-wise manner y(t) is then of an exponential configuration.

Figure 6:
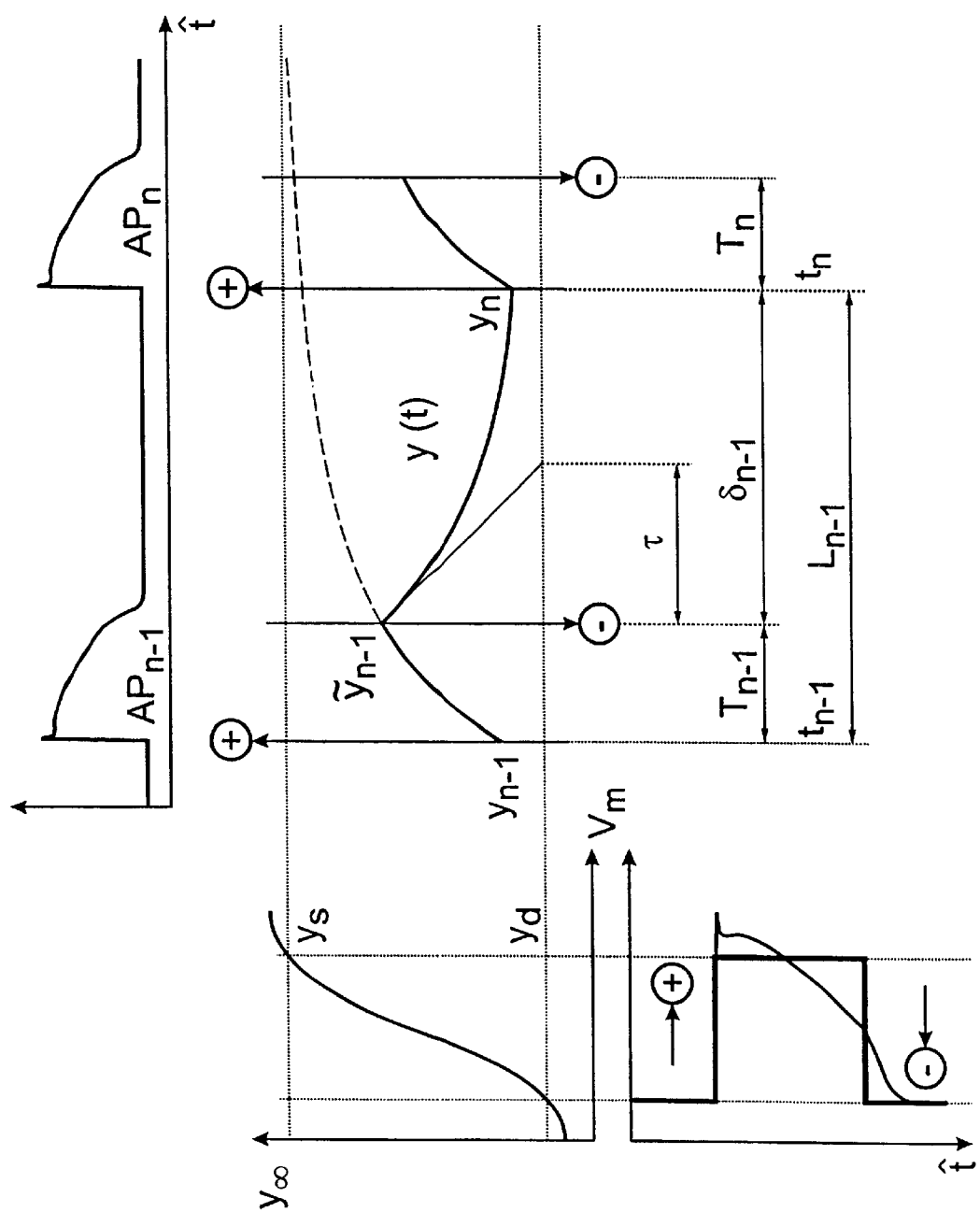
FIG. 6 is a graphical depiction of a model gate variable simulation according to the present invention.
Figure 7B:
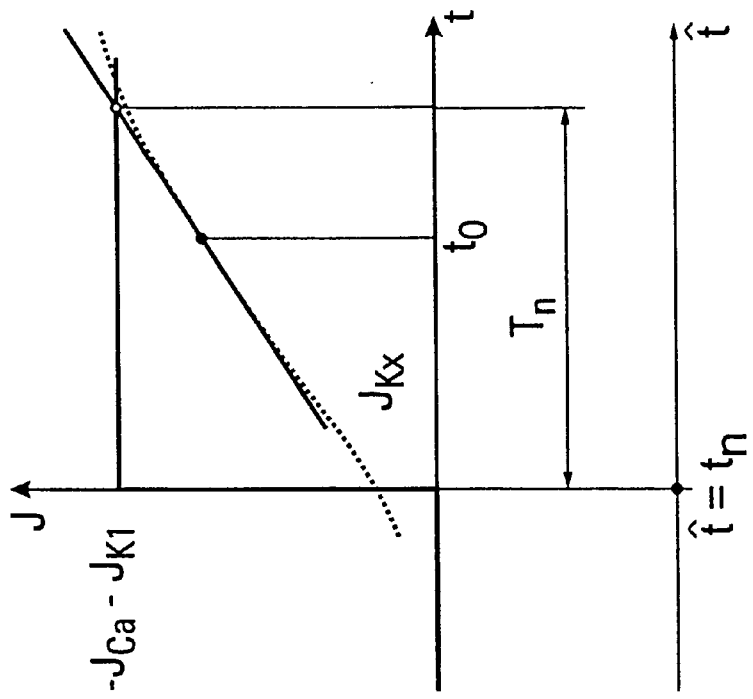
FIG. 7b is a graphical depiction of an ion current simulation according to the present invention.
Figure 7A:
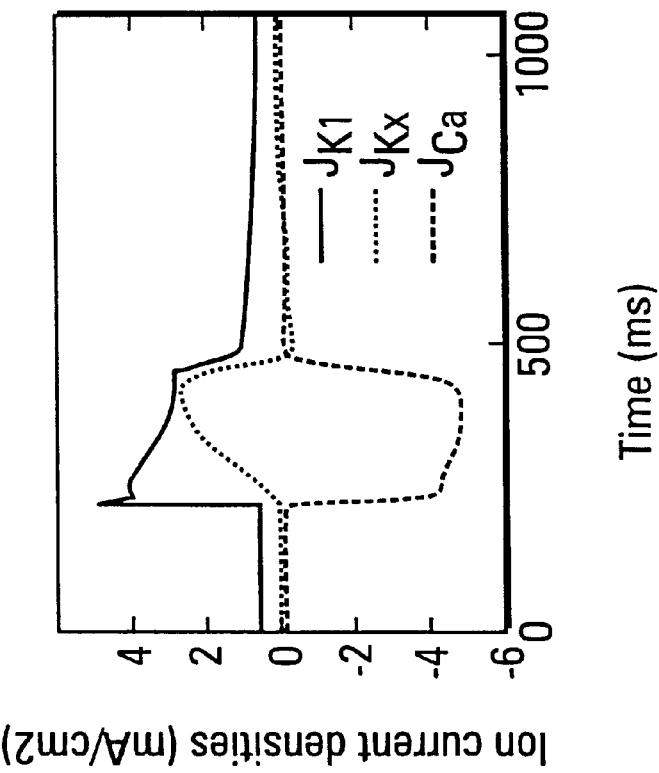
FIG. 7a is a graphical depiction of an ion current simulation according to the present invention.

These considerations, which form the basis for the model approach, are outlined in FIG. 6. In this example, y represents an approximation of the gate variable x (the conformity with FIG. 4 should be noted).

In the specific case of the cell, the repolarization time is represented by the action potential duration, which for the sake of simplicity is identified by T in the calculations. For derivation purposes, it is more appropriate, in place of the heart rate, to refer to the reciprocal value, that is to say the cycle length L (stimulation period). The duration of the diastole is denoted by δ. If the index of these values denotes the number of the respective action potential, then the following applies:

$$L_v = T_v + \delta_v \quad (4)$$

The solution of the initial value problem described in Equation (2) then gives the following for the edge points of the systolic interval ($T_{n-1}$) and the diastolic interval ($\delta_{n-1}$) (FIG. 6):

$$\begin{cases} y_{n-1}^\% = (y_{n-1} - y_s)e^{-\frac{T_{n-1}}{\tau}} + y_s \\ y_n = (y_{n-1}^\% - y_d)e^{-\frac{\delta_{n-1}}{\tau}} + y_d \end{cases} \quad (5)$$

Accordingly, the y-initial values of two successive cycles (n−1 and n) are related in the following fashion:

$$y_n = (y_{n-1} - y_s)e^{-\frac{L_{n-1}}{\tau}} + (y_s - y_d)e^{-\frac{L_{n-1} - T_{n-1}}{\tau}} + y_d \quad (6)$$

Using Equation (6), the following (approximate) relationships result for the gate variables x and f:

$$x_n = (x_{n-1} - x_s)e^{-\frac{L_{n-1}}{\tau_x}} + (x_s - x_d)e^{-\frac{L_{n-1} - T_{n-1}}{\tau_x}} + x_d \quad (7a)$$

$$f_n = (f_{n-1} - f_s)e^{-\frac{L_{n-1}}{\tau_f}} + (f_s - f_d)e^{-\frac{L_{n-1} - T_{n-1}}{\tau_f}} + f_d \quad (7b)$$

Next, the reference of those state variables to the action potential duration must be derived. For that purpose, it is helpful to analyze the variation of time of the most important ion currents of the cell model in order to define a mathematical criterion for triggering repolarization in the action potential. The ion currents which are relevant in relation to repolarization are: 1) the Ca-current and 2) the currents through the dynamic and the static K-channel, the total flow of which is directed outwardly of the cell during the rel) olarization phase. These currents are involved in the calculation in the form of the current densities $J_{Ca}$, $J_{Kx}$ and $J_{kl}$. In contrast, the Na-current is negligible as apart from during depolarization it is almost zero.

During repolarization the resulting membrane current is directed outwardly of the cell; and the following applies:

$$J_{Ca} + J_{Kl} + J_{Kx} > 0 \quad (8)$$

In particular, on the assumption that the action potential here is approximated as a rectangular pulse (Equation (3)), the current densities $J_{Ca}$ and $J_{kl}$ (that is to say also the total thereof are approximately constant during the plateau phase.

It will be appreciated, however, that in the case of the Ca-channel the value of these constants still depends on the open state of the inactivation gate (f) at the beginning of the action potential. The general approaches used may therefore simplified as follows:

$$J_{Ca} \approx -f_n A_{Ca} \quad (9a)$$

$$J_{Kl} \approx A_{Kl} \quad (9b)$$

$$J_{Kx} \approx X_x(t) A_{Kx} \quad (9c)$$

In this case, $J_{Kx}$ alone is still variable with respect to the time during the plateau phase, and therefore determines when the current direction changes. The range of applicability of Equations (9a, 9b and 9c) is limited to the plateau phase (diastole). The fact that, by virtue of that simplified representation of the ion currents, the total current and thus $dV_m/dt$ during the plateau phase is not equal to zero, that is to say the action potential plateau in strict terms cannot be flat (as described by Equation (3)), must be tolerated as a consequence of these simplifications. Ultimately, the duration (pulse width) of the action potential is of interest, and not the precise signal morphology.

In this case, the moment of current equilibrium, which is defined by the following equation, is to be viewed as the repolarization time:

$$(J_{Ca} + J_{Kl} + J_{Kx})|_{t=T_n} = 0 \quad (10)$$

If the simplified expressions for the ion currents from Equation (9) are put into the repolarization condition from Equation (10), the result is the following equation:

$$x^2(T_n) - c_1 f_n + c_0 = 0 \quad (11)$$

with $$c_1 = \frac{A_{Ca}}{A_{Kx}}; \quad c_0 = \frac{A_{Kl}}{A_{Kx}}, \quad (11b)$$

which is to be solved for $T_n$, the action potential duration of the cycle n being considered.

The time-variable value x(t) is a solution to an equation of the form of Equation (2), which under the specified framework conditions of Equation (9) assumes the configuration of a linear differential equation of the first order, as follows:

$$x(t) = (x_n - x_s) e^{-\frac{t}{\tau_x}} + x_s \text{ for } 0 \le t \le T_n; t = \hat{t} - t_n \quad (12a)$$

and $$x^2(t) = (x_n - x_s)^2 e^{-\frac{2t}{\tau_x}} + 2x_s(x_n - x_s) e^{-\frac{t}{\tau_x}} + x_s^2 \quad (12b)$$

It will be seen from FIGS. 8a and 8b that $J_{Kx}$ extends linearly with a good degree of approximation in the considered time interval of the systole. To further simplify the calculation, it is permissible to implement linearization of the approach for $J_{Kx}$ at a point $t=t_0$. With:

$$x^2(t) \approx (x_n - x_s)^2 \eta^2 + 2x_s(x_n - x_s) \eta + x_s^2 - \frac{2\eta}{\tau_x}[(x_n - x_s)^2 \eta + x_s(x_n - x_s)](t - t_0) \quad (13)$$

there follows:

$$x^2(t) \approx (a_2 x_n^2 + a_1 x_n + a_0) \frac{t}{\tau_x} + (b_2 x_n^2 + b_1 x_n + b_o) \quad (14)$$

where:

$$\eta = e^{-\theta_0}; \theta_0 = \frac{t_0}{\tau_x} \quad (15)$$

and:

$$\begin{cases} a_2 = -2\eta^2 \\ a_1 = -2x_s \eta(1 - 2\eta) \\ a_0 = 2x_s^2 \eta(1 - \eta) \end{cases} \begin{cases} b_2 = \eta^2(1 + 2\theta_0) \\ b_1 = 2x_s \eta(1 - \eta) + 2\theta_0 x_s \eta(1 - 2\eta) \\ b_0 = x_s^2(1 - \eta)^2 - 2\theta_0 x_s^2 \eta(1 - \eta) \end{cases} \quad (16)$$

If the above approach is adopted: $t_0 = \tau_x/2$ (for example $t_0=150$ ms), then the linearization point, under physiological conditions, is certain to lie within the plateau phase of the action potential. Common values of the action potential duration (T) are approximately between 100 ms and 400 ms (frequently T≈200 ms), while $\tau_x$ in the excited state of the cell can assume values of between 100 ms and 300 ms. Under the simplifying assumptions involved, however, $\tau_x$ is to be viewed as a constant whose value lies within that possible range. Admittedly, these assumptions concerning T and $\tau_x$ apply only as long as, normal functionality of the cell can be presupposed.

Using the approximation Equation (14), which is also used in Equation (11a), together with Equation (7a,b) gives the following relationships:

$$\begin{cases} T_n = \tau_x c_1 f_n - c_0 - \frac{(b_2 x_n^2 + b_1 x_n + b_0)}{a_2 x_n^2 + a_1 x_n + a_0} \\ x_n = (x_{n-1} - x_s) e^{-\frac{L_{n-1}}{\tau_x}} + (x_s - x_d) e^{-\frac{L_{n-1} - T_{n-1}}{\tau_x}} + x_d \\ f_n = (f_{n-1} - f_s) e^{-\frac{L_{n-1}}{\tau_f}} + (f_s - f_d) e^{-\frac{L_{n-1} - T_{n-1}}{\tau_f}} + f_d \end{cases} \quad (17,a,b,c)$$

which starting from the initial values:

$$(T_0, x_0, f_0) \quad (17D)$$

completely describe the system behavior in terms of the properties which are of interest (although admittedly, on the basis of simplifying assumptions).

This mathematical modeling represents an important part of the desired system identification, the equations of which express the non-linear dynamic relationship between the state values: action potential duration (T), and the gate variables x and f. In that respect, the input signal of the system is the cycle length L. The model parameters $\tau_x$, $c_1$ and $c_0$ are to be emphasized as the most important values in terms of early detection of arrhythmia phenomena. In that respect $\tau_x$ represents the time constant of the dynamic K-channel, while $C_1$ and $c_0$, in accordance with their definition in Equations (11b,c), express the ratios of the Ca- and K-current amplitudes. Ultimately, the Ca- and K-current amplitudes are a measurement of the conductivities of the ion channels in question and afford information about the working points thereof.

In contrast, to the cell model used in the literature, the system description summarized stands for a discrete substitute model of the cell describing the dependency of the action potential duration on the stimulation frequency. The otherwise continuous state values: x and f, are here represented by the numerical sequences $X_n$ and $f_n$, which respectively represent the initial values of the continuous parameters in question at the beginning of each action potential.

With knowledge of the physiological model parameters and the state vector corresponding to an action potential, it is now possible to calculate the duration of the next action potential. This recursive rule of calculation also provides proof of the "memory" effect of the heart muscle cell, which is often discussed in the literature. However, how far the memory measurably extends into the past depends on the specific system parameters involved.

Derivation of the Steady State APD(HR)-curve

Although we now have a complete system description, reverse calculation of the cell parameters, which are intended to provide information about the arrhythmogenetic state of the substrate, is still not possible in that form. Only the cycle length L and the repolarization time (in the form of the APD, the QT-time or similar values) are measurable at clinically viable cost. The model equations (17a to 17d), however, also include internal values (gate variables x and f), which are not accessible in terms of measurement procedure. It is necessary, then, to eliminate these internal values.

For that purpose, the system is considered in a steady state, i.e., when it has already been stimulated at a constant frequency for a relatively long time so that transient events are terminated. It is admittedly apparent from FIG. 3a that action potential duration of the cell has an internal limit cycle; this, however, is to be disregarded in the derivation procedure. As the process according to the current invention is to supply indications of an incipient arrhythmia when there is still no significant rise apparent in the heart rate, it is possible to forego the gate variable f as a state variable. More specifically, if the cycle length is sufficiently great (stimulation frequency correspondingly low), then f is already in a steady state at the beginning of each action potential and is approximately of the value $f_n=1$. It is also known from investigations on cell models that the diastolic asymptotic value of the x-variable (Xd) is approximately zero, and $x_n$ as the initial value of x at the beginning of the action potential (in particular at stimulation rates which are not excessively high) is substantially less than 1. The simplifications which arise as a result are mathematically formulated in the following terms:

Limit cycles disregarded (steady state)

$$\Rightarrow \begin{cases} x_n \approx x_{n-1} = \hat{x} \\ T_n \approx T_{n-1} = T(=APD) \\ L_n \approx L_{n-1} = L \end{cases} \quad (18a)$$

$$f_n \approx 1 \rightarrow g = c_1 - c_0 = (A_{Ca} - A_{Kl})/A_{Kx} \quad (18b)$$

$$X_d \approx 0 \quad (18c)$$

$$x_n \ll 1 \rightarrow x_n^2 \approx 0 \quad (18d)$$

Accordingly, the following results from (17b):

$$\hat{x} = \frac{x_s}{e^{\frac{L}{\tau_x}} - 1} \left( \frac{T}{e^{\tau_x} - 1} \right) \quad (19)$$

In the aim of arriving at the dependency between T and L, i.e., to describe in formula terms an APD(HR)|-curve that can be determined by a measuring procedure, it is meaningful to linearly approximate relationship (19). It is possible, in that way, for T to be explicitly expressed. Linearization is effected at the place where $T=T_1$, so that a value of the action potential duration, which is to be physiologically expected, is to be used at that point (for example $T_1=200$ ms). In such a case, the following approximation applies:

$$e^{\frac{T}{\tau_x}} - 1 \approx e^{\theta_1} - 1 + \frac{e^{\theta_1}}{\tau_x}(T - T_1) \quad (20a)$$

making the following substitutions:

$$\theta_1 = \frac{T_1}{\tau_x}; a = e^{\theta_1}; \beta = e^{\theta_1}(1 - \theta_1) - 1; \quad (20b)$$

$$\xi = \frac{x_s}{e^{\frac{L}{\tau_x}} - 1}; \lambda = \frac{T}{\tau} \quad (20c)$$

results in the following:

$$\hat{x} \approx \xi(a\lambda + \beta) \quad (21)$$

Inserting Equation (21) into Equation (17a) gives:

$$\lambda = \frac{g - b_1 \xi(a\lambda + \beta) - b_0}{a_1 \xi(a\lambda + \beta) + a_0} \quad (22)$$

or expressed in a different fashion:

$$\lambda^2 + k_1\lambda + k_0 = 0 \quad (23)$$

with $$k_1 = \frac{\beta}{a} + \frac{b_1}{a_1} + \frac{a_0}{a_1\xi a}; \quad (24a,b)$$

$$k_0 = \frac{\beta}{a} \cdot \frac{b_1}{a_1} + \frac{b_0 - g}{a_1\xi a}$$

The quadratic Equation (23) is to be solved in consideration of $\lambda$ being real and $\lambda>0$. When consideration is given to the coefficient values and the variation limits under physiological conditions the solution is as follows:

$$\lambda = \frac{1}{2}\left(\sqrt{k_1^2 - 4k_0} - k_1\right) \quad (25)$$

There is still the danger that, in the worst case scenario, the solution can turn out to be of a complex value. That possibility, however, cannot be settled at viable cost on the basis of a parameter discussion, it must therefore be taken into consideration when developing the algorithms and must be settled by numerical measures.

By reverse substitution, Equation (25) gives the following:

$$T = \tau_x \left\{ \sqrt{\left[a\left(e^{\frac{L}{\tau_x}} - 1\right) + b\right]^2 - \left[c\left(e^{\frac{L}{\tau_x}} - 1\right)(b_0 - g) + d\right]} - \left[a\left(e^{\frac{L}{\tau_x}} - 1\right) + b\right] \right\} \quad (26)$$

-continued with:

$$a = \frac{1}{2} \cdot \frac{1-\eta}{2\eta-1} e^{-\theta_1} \quad b = \frac{1}{2}\left(1 - \theta_1 - e^{-\theta_1} + \frac{1-\eta}{2\eta-1} - \theta_0\right) \quad (27a,b)$$

$$c = \frac{1}{2x_s^2} \cdot \frac{e^{-\theta_1}}{\eta(2\eta-1)} \quad d = (1 - \theta_1 e^{-\theta_1}) \cdot \left(\frac{1-\eta}{2\eta-1} - \theta_0\right)$$

from which finally the explicit relationship between the action potential duration (T) and the cycle length (L) results as follows:

$$T(L, \tau_x, g) = \tau_x \left(\sqrt{\frac{m_1 e^{\frac{2L}{\tau_x}} + m_2 e^{\frac{L}{\tau_x}} + m_3 g e^{\frac{L}{\tau_x}} +}{m_4 g + m_5 + m_6 e^{\frac{L}{\tau_x}} + m_7}}\right) \quad (28)$$

with, $m_1 = a^2$; $m_2 = -2a^2 + 2ab - cb_0$; $m_3 = c$; $m_4 = -c$; $m_5 = (a-b)^2 + cb_0 - d$; $m_6 = -a$; and $m_7 = a - b$.

Parameters in that relationship are $\tau_x$, the time constant of the dynamic K-channel, and g, an expression which, on the basis of Equation (18b) and (11a,b), describes the relationships between the levels of permeability of the Ca- and the K-channels. Thus, it is possible to calculate back to parameters from the ion channels whose key role in the process of arrhythmogenesis has already been confirmed by experimental electrophysiological studies.

However, the action potential duration is not queried as a function of the associated cycle length—those values are measurable and thus known—instead the physiological parameters $\tau_x$ and g which characterize the state of the substrate are queried. The non-linear and transcendent linking of those values in Equation (28), however, gives rise to difficulties in terms of the intention of determining the values thereof.

Figure 8:
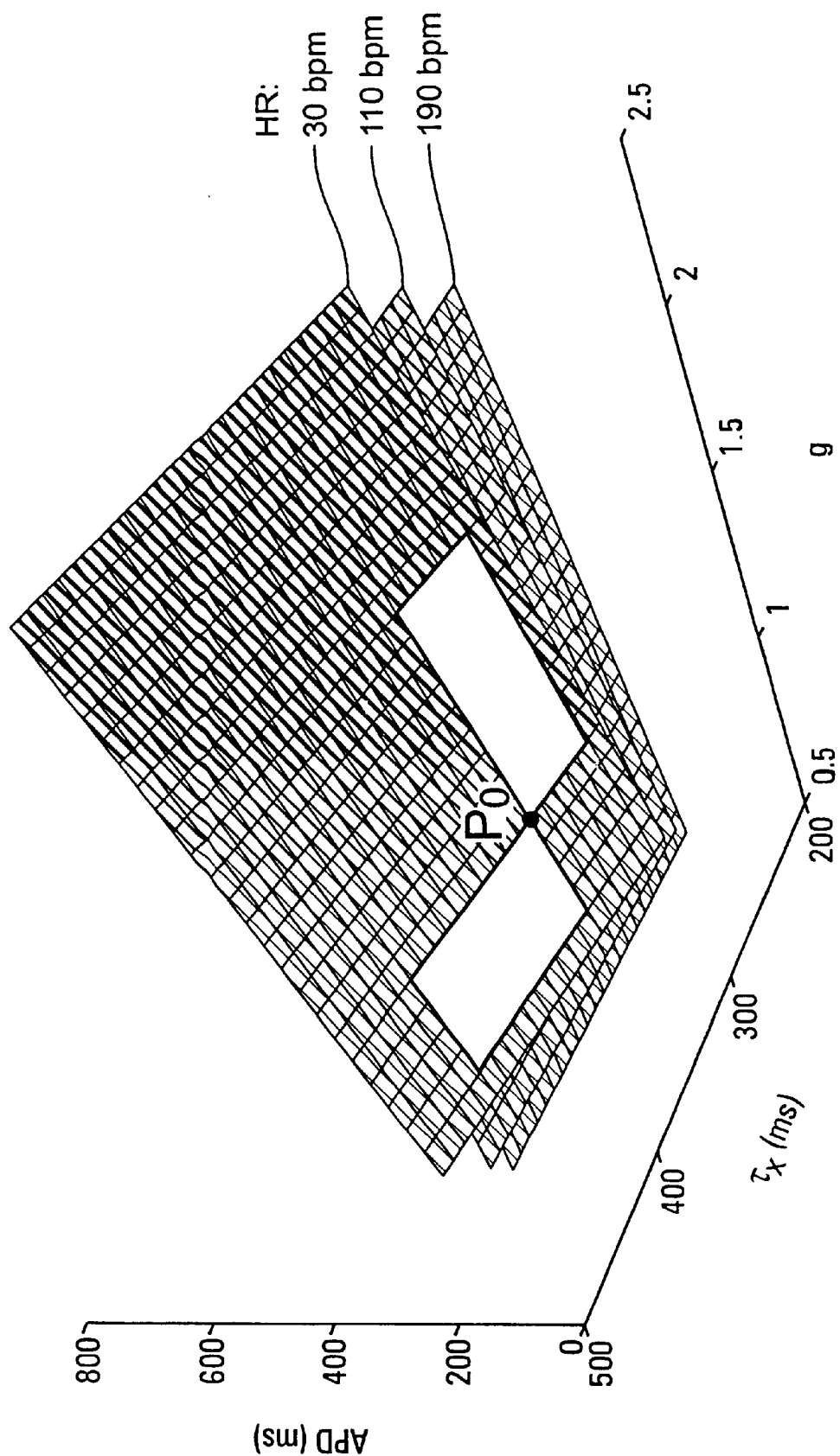
FIG. 8 is a graphical depiction of the dependency of the action potential duration on physiological parameters according to the present invention.

FIG. 8 shows the dependency of the action potential duration T on the physiological parameters $\tau_x$ and g in the form of a family of areas whose family parameter is the stimulation frequency. It will be seen on the tangential plane at point $P_0 = (\tau_{x0}, g_0)$, that these areas are admittedly slightly curved, but a linearized description adequately approximates that relationship. It is this fact that justifies linearization in Equation (28) with respect to the parameters $\tau_x$ and g. More specifically, the values of these parameters can be calculated, based on a linear equation system.

To calculate these values, it is necessary to ascertain the partial differential coefficients of the function $T(L, \tau_x, g)$ with respect to the parameters $\tau_x$ and g:

and the value of the function at point $P_0 = (\tau_{x0}, g_0)$:

$$T_0(L) = \tau_{x0}\left(\sqrt{\frac{m_1 e^{\frac{2L}{\tau_{x0}}} + m_2 e^{\frac{L}{\tau_{x0}}} + m_3 g_0 e^{\frac{L}{\tau_{x0}}} +}{m_4 g_0 + m_5 + m_6 e^{\frac{L}{\tau_{x0}}} + m_7}}\right) \quad (30)$$

In the linearized form, therefore, the relationship between the action potential duration and the cycle length thus reads as follows:

$$T(L, \tau_x, g) \approx T_0(L) + \left.\frac{\partial T}{\partial \tau_x}\right|_{\tau_{x0}, g_0} \cdot (\tau_x - \tau_{x0}) + \left.\frac{\partial T}{\partial g}\right|_{\tau_{x0}, g_0} \cdot (g - g_0) \quad (31)$$

Equation 31 represents hereinafter the basis for the development of an algorithm for determining the parameters $\tau_x$ and g, i.e., the values which afford information about the functional state of the Ca- and K-channels in terms of a threatening arrhythmia.

Measurement Rules and Draft of an Algorithm for Parameter Extraction

As already mentioned, the values to be measured are the cycle length L and the repolarization time T (viewed in quite general terms). These values are to be extracted over a time portion of a plurality of heart beats (at least 2) from the intracardial measurement signal. M pairs of values are formed therefrom as follows:

$$(L_m, T_m) \quad (32)$$

where the index m identifies the serial number within the set of values (method=1 . . . M). In accordance with one embodiment of the current invention, the measurement signal is to have he following properties:

With regard to sampling frequency: a sampling frequency of 1000 Hz is to be utilized, particularly with regard to the algorithm for signal measurement. However, if it is assumed that it is possible to approach the measurement error caused by the distribution of white noise, a sampling frequency of at least 500 Hz is still acceptable. In any case, as described $$\left.\frac{\partial T}{\partial \tau_x}\right|_{\tau_{x0}, g_0} = \left(\sqrt{m_1 e^{\frac{2L}{\tau_{x0}}} + m_2 e^{\frac{L}{\tau_{x0}}} + m_3 g_0 e^{\frac{L}{\tau_{x0}}} + m_4 g_0 + m_5 + m_6 e^{\frac{L}{\tau_{x0}}} + m_7}\right) + \quad (29a,b)$$

$$-\frac{L}{\tau_{x0}}\left(\frac{2 m_1 e^{\frac{2L}{\tau_{x0}}} + m_2 e^{\frac{L}{\tau_{x0}}} + m_3 g_0 e^{\frac{L}{\tau_{x0}}}}{2\sqrt{m_1 e^{\frac{2L}{\tau_{x0}}} + m_2 e^{\frac{L}{\tau_{x0}}} + m_3 g_0 e^{\frac{L}{\tau_{x0}}} + m_4 g_0 + m_5}} + m_6 e^{\frac{L}{\tau_{x0}}}\right)$$

$$\left.\frac{\partial T}{\partial g}\right|_{\tau_{x0}, g_0} = \tau_{x0} \frac{m_3 e^{\frac{L}{\tau_{x0}}} + m_4}{2\sqrt{m_1 e^{\frac{2L}{\tau_{x0}}} + m_2 e^{\frac{L}{\tau_{x0}}} + m_3 g_0 e^{\frac{L}{\tau_{x0}}} + m_4 g_0 + m_5}}$$

hereinafter, the equation system for determining the parameters is resolved on the basis of the least error squares method. That is to say, a relatively large number of pairs of measurement values is calculated, with errors being averaged out (white noise). If the aim is optimization of the processes in terms of calculation time, a level of time resolution of the signal, which is as accurate as possible, is advantageous, as that reduces the need for signal preprocessing.

With regard to amplitude resolution: in itself only the time information is of interest. However, the repolarization time must be ascertained by suitable signal processing, that question can be more accurately answered only when both the measurement signal used and also the evaluation algorithms are established. For that purpose, a series of clinical measurements are first required as the basis for the development of those algorithms. For signals which can in practice be detected by the implant (for example IEGM, coronary sinus signal), it is necessary to clarify which signal type is most suitable. As it will be noted, however, that amplitude resolution adversely affects the level of accuracy in terms of determining the moment of repolarization, as such it is not possible to use a level of resolution of less than 8 bits.

If we consider the requirement of Equation (18b), then the time intervals during which the pairs of measurement values $(L_m, T_m)$ are detected are to be so selected that a steady state prevails. That admittedly is easy to establish on the basis of variability of the heart rate, but as the simulation results set forth hereinafter show, it is already sufficient if the measurement parameters do not change excessively or suddenly (e.g., rate of change of the heart rate<10 bpm/heart rate).

Based on the pairs of measurement values $(L_m, T_m)$, using Equation (31), the following linear equation system is formed:

$$u_{0,m}\tau_x + v_{0,m}g = w_{0,m}; m=1 \ldots M; M \geq 2 \quad (33a)$$

with $$u_{0,m} = \left.\frac{\partial T}{\partial \tau_x}\right|_{\tau_{x0}, g_0} = u_0(L_m) \quad (33b,c,d)$$

$$v_{0,m} = \left.\frac{\partial T}{\partial g}\right|_{\tau_{x0}, g_0} = v_0(L_m)$$

$$w_{0,m} = w_0(L_m) = T_m - T_0(L_m) + u_0(L_m)\tau_{x0} + v_0(L_m)g_0$$

the solution to which gives the parameter set $(\tau_x, g)$. This calculation requires two pairs of measurement values $(L_m, T_m)$ which lead to linearly independent equations.

Because of the above-mentioned limit cycles of the action potential duration and because a measurement would also inevitably involve error, there is the advantageous alternative of taking more than just two pairs of measurement values (for example M=100). Accordingly, Equations (33a to 33d) is an over-defined equation system, the resolution of which is effected on the basis of the least error squares method. This property implicitly affords an averaging so that freak values do not significantly affect the parameter determining procedure. This property also explains why the requirement that the measurement signals be steady is in relative terms, more specifically because overshoots as a result of a sudden frequency jump are averaged out.

A further improvement is achieved by virtue of the algorithm being of an iterative configuration for the parameter extraction procedure. To establish and resolve Equation system (33) it is necessary to present an estimation solution $(\tau_{x0}, g_0)$ for the parameters, i.e., the point of contact Po of the tangential plane.

These estimated values can be derived from physiological considerations or from experience. As the tangential plane still well approximates the surface in FIG. 8 over relatively wide ranges, it is possible in the zero approximation $(\tau_{x0}, g_0)$ to use values corresponding to the healthy state, without adversely affecting the accuracy of the solution. Nonetheless, it is advantageous for the degree of accuracy of the solution to be iteratively improved. Based on the starting solution $(\tau_{x0}, g_0)$, the coefficients of the Equation system (33) are determined, and the solution $(\tau_x, g)$ is ascertained therefrom. The approximation now serves as the starting solution for the next iteration operation.

Two facts serve as interrupt criteria to iteration operation: 1) either that the solutions (in the sense of the $L_2$-standard) to the equation differ by less than the required threshold value; or 2) that the number of iterations exceeds a predetermined acceptable value. The second criterion in particular ensures that, in the case of divergent behavior, the algorithm does not go into an endless loop. If the iteration breaks down by virtue of the second criterion, no solution occurs. As already mentioned in the discussion of Equation (25), which appears here in Equation (33d), care must be taken to ensure that the solution does not assume complex values. More specifically, in the case of an unfavorable set of measurement data where no physiologically meaningful solution was found for $\tau_x$ and g a fresh set of measurement data has to be selected.

Finally, FIGS. 9a, 9b and 9c show an example of the use of this parameter estimation algorithm. FIGS. 9a and 9b show the heart rate (HR) (representative here for L) for which a random but physiologically viable pattern was assumed to apply. The repolarization time (here in the form of APD) was simulated based on the model description in Equation (18). The initial values of the state variables correspond to a steady state at a stimulation frequency of 70 bpm ($x_0$=0.0348, $f_0$=0.9999, and $T_0$=239.5 ms).

The two trend values (HR and T), which in clinical practice first have to be extracted from a suitable intracardial measurement signal as numerical sequences, represent the input values of the estimation algorithm. FIG. 9c plots the APD(HR)| -curve which results from Equation (28). Parameters of that curve are the reverse-calculated cell parameters $(\tau_x, g)$. Therefore, the morphology of this curve affords information about the cellular functional state.

In order to afford a view of the quantitative nature of the solution, reference will be made to the following numerical example. In the specific case (FIGS. 9a, 9b and 9c), the parameters $\tau_x$=158 ms and g=0.65 were predetermined for forward simulation in accordance with Equations (18), while $\tau_{x0}$=200 ms and $g_0$=0.5 are applied as starting values for the iterative reverse calculation. The values $\tau_x$=160.6788 ms and g=0.6366 were obtained within 3 iterations as a result of the parameter estimation procedure.

Model Calculations for Testing the Process

In order to demonstrate by model technology the efficiency and power of the described algorithm, adequate test environments are constructed hereinafter as a basis for a quantitative assessment. In this respect, reverse parameter calculation is investigated both with relation to the equivalent model and also to the physiologically complete cell model. Approximations were effected a plurality of times, on the basis of the equivalent model Equation (18), so that firstly the accuracy of the process has to be checked. The approximations are implemented on the equivalent model as it is solely thereon that this question can be assessed under defined boundary conditions (the equivalent model was the starting point for drawing up the parameter estimation process).

Both stochastic and also deterministic heart rate patterns are predetermined for the tests. The operation of ascertaining the associated APD-values is effected on the basis of the recursion formulae from Equation (18) and the same initial values as in the above section. Therefore, the heart rate starts in each case from 70 bpm, with the variation thereof in these tests being limited to 70±10 bpm. The background of this measure is checking whether the process also functions in the event of minor deflection of the system, i.e. the aim is to find out whether natural variations in the heart rate are sufficient (even without an explicit loading or stress on the patient). The simulations were systematically implemented for numerous predetermined parameter combinations ($\tau_x$, g) whose range of variations (based on values in the literature) and patterns are to be found in FIG. 10.

First, the process was tested at a deterministically predetermined heart rate pattern in the form of a ramp at between 60 bpm and 80 bpm. In practice, this means that the pacemaker must follow a stimulation protocol in order to deflect the system. Under these framework conditions, the parameter reverse calculation is distinguished by relative errors of below 2%, and where only three iterations are required. In the case of the stochastically stimulated system, relative errors of up to 5% have to be reckoned with, in which respect it may occasionally also occur that, by virtue of a precisely unfavorable set of measurement values, no physiologically meaningful result (for example a complex value) is achieved. The number of iterations required is illustrated (in dependence on the specific parameter values) in FIG. 10. It is to be noted in principle that the operation of determining the parameter g (even with deterministic heart rate patterns) involves less error than that required for the time constant $\tau_x$.

The simulation results show that, even with stochastic heart rate patterns which are close to the natural ones, useable results are still achieved. It is therefore not absolutely necessary, for system identification purposes, to rigidly follow a specific predetermined stimulation protocol, which may not correspond to the instantaneous demands of the organism. In this sense the implant predominantly performs the function of a diagnostic observer and implements a therapeutic measure only when required.

Test of the Process on the Physiological Cell Model

In this section, the process is investigated under working conditions which are close to reality. The test object, or system to be identified, used is a cell model (based on the cell models of the literature) whose state variables directly depict physiological parameters. It is possible in this way to reproduce a pathological system behavior in direct relationship to clinical studies by a simulation procedure.

Figure 10:
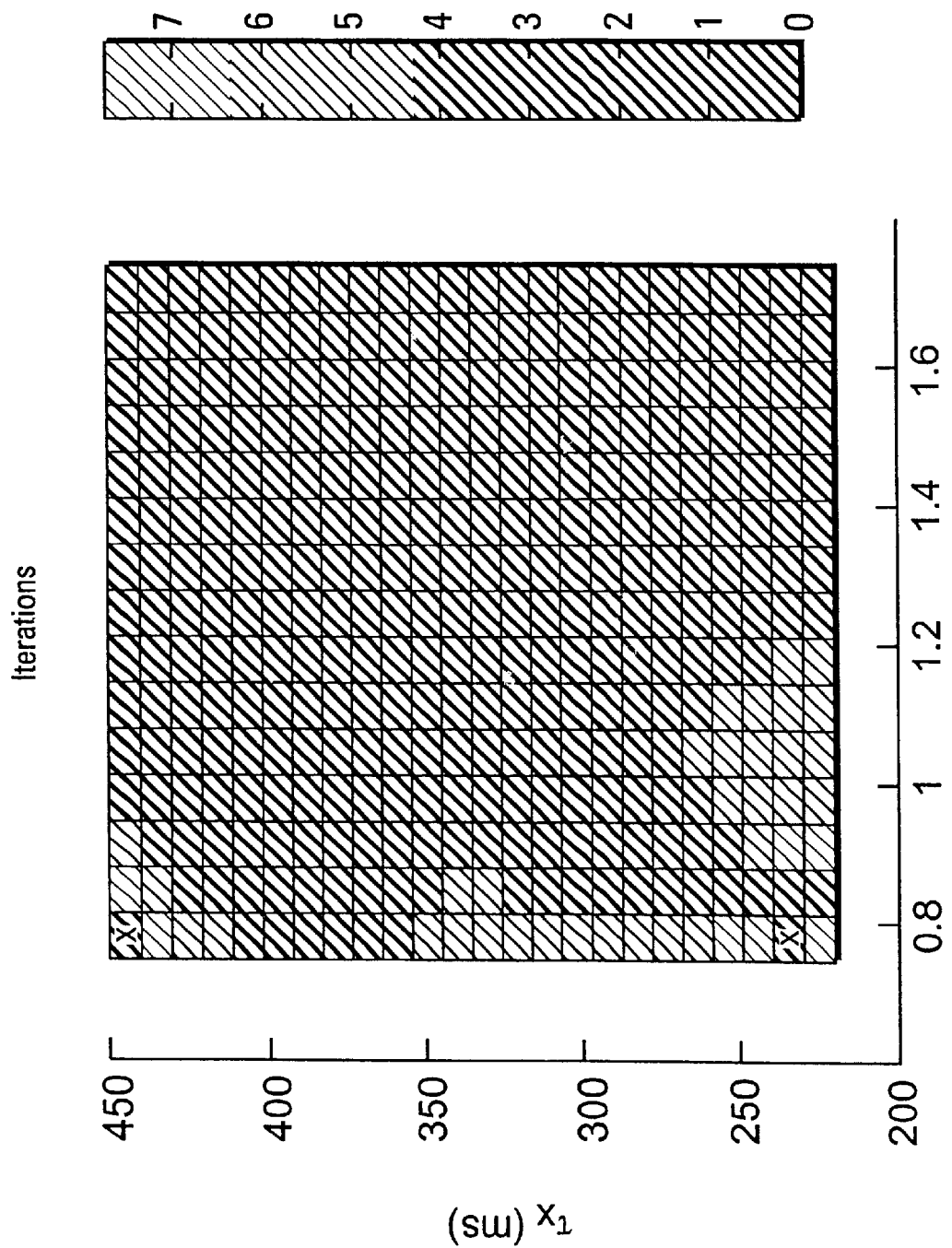
FIG. 10 is a graphical depiction of predetermined parameter combinations according to the present invention.
Figure 11A:
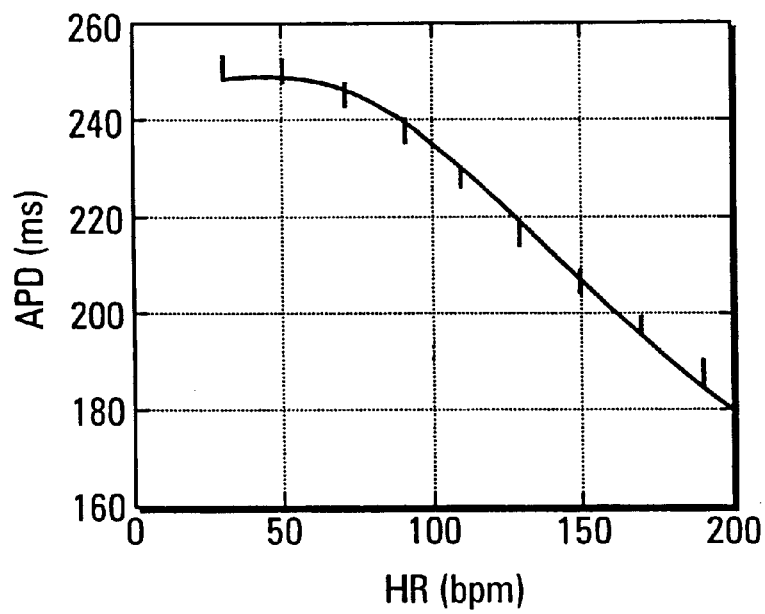
FIG. 11a is a graphical depiction of an APD and HR simulation according to the present invention.
Figure 11B:
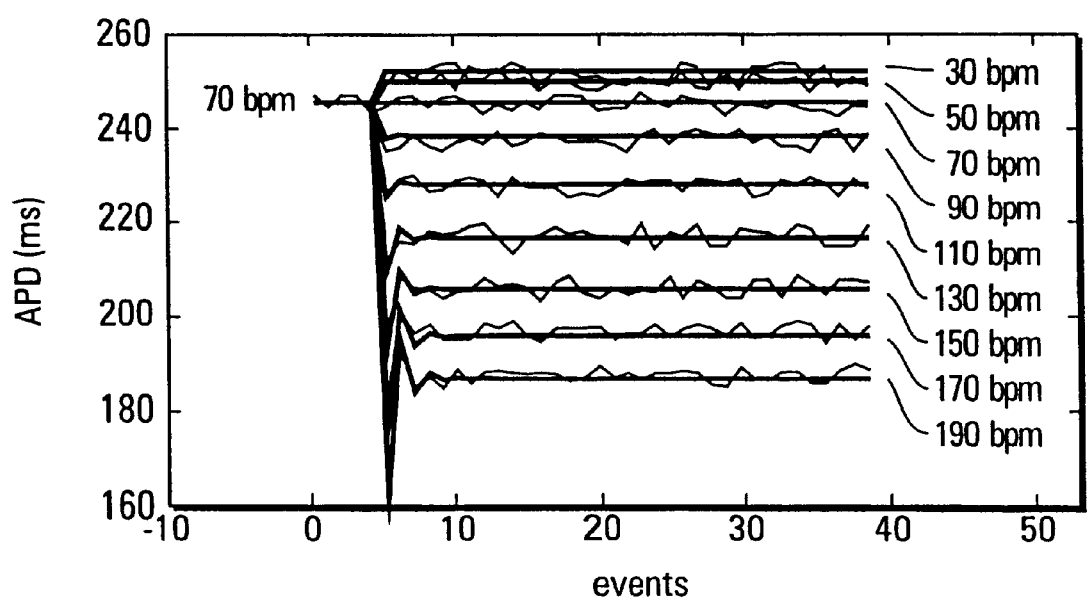
FIG. 11b is a graphical depiction of a transient process simulation according to the present invention.

First, the fundamental relationship between the parameters APD and HR which are the starting point for system identification is investigated. FIGS. 10 and 11 show this relationship for the physiological cell model, on the basis of two stimulation protocols. FIGS. 11a and 11b illustrate the reaction of the system to a sudden change in the stimulation frequency. In FIG. 11a, the pairs of measurement values (HR, APD) (corresponding to Values (32)) were plotted as points (groups comprising a plurality of pairs of measurement values for the respective stimulation frequency after the jump). The solid line in contrast represents the APD (HR)| -curve, which is calculated therefrom (by way of ($\tau_x$, g)) and which displays the result of the system identification. FIG. 11b shows the transient process itself for both the physiological cell model and the equivalent model. In this respect, the parameter values ($\tau_x$, g), which are necessary for the equivalent model, were calculated back from the measurements on the physiological model. FIG. 11b shows in particular how the equivalent model reproduces even the transient process and that in spite of simplifications it also has in quantitative terms a physiologically correct behavior.

As an important piece of information from FIG. 11b, it is to be stressed that the oscillations of the action potential duration shortly after the jump are predominantly attributable to the dynamic transient process (which even the equivalent model reproduces), while the oscillations in the further course of the pattern are caused by the internal limit cycle. To put this another way, this study clearly shows how pronounced the above-mentioned memory of the cell is and it diagrammatically indicates a procedure for measuring same. Although from a theoretical point of view recursive systems have an infinitely long memory, in a specific situation the cell memory, which can be measured in practice (at least in regard to the phenomena being considered here), is limited to about 6–7 cycles. This memory number represents the number of significant overshoots of the APD after the frequency jump (FIG. 11b).

Figure 12A:
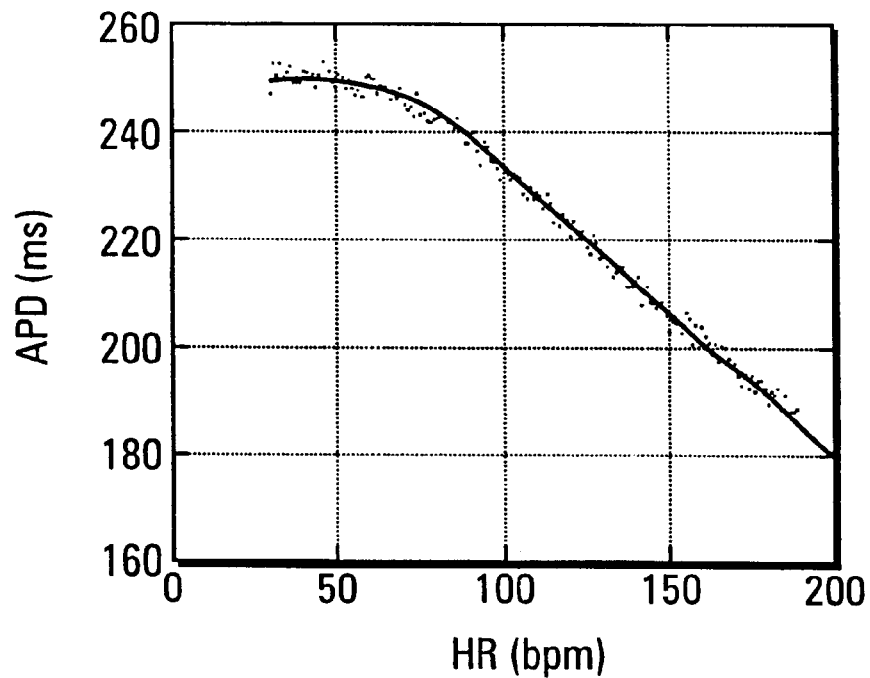
FIG. 12a is a graphical depiction of an APD and HR simulation according to the present invention.
Figure 12B:
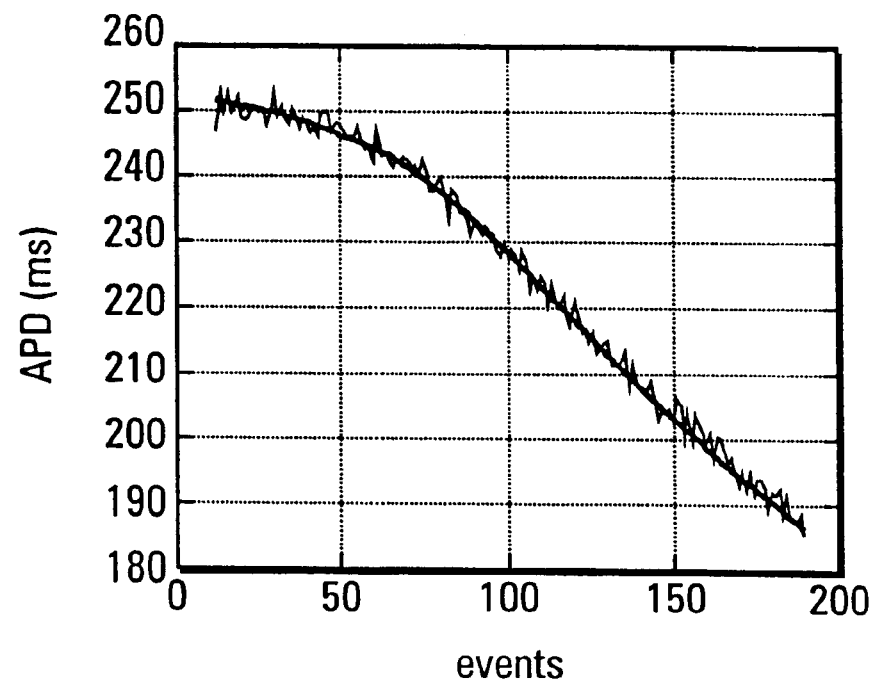
FIG. 12b is a graphical depiction of a transient process simulation according to the present invention.

FIGS. 12a and 12b show a further test of the equivalent model and shows that the model also behaves physiologically correctly under other framework conditions. The protocol used to excite the system in this test involves a stimulation frequency configuration which rises in a ramp form. In regard to the illustrated parameters, FIGS. 12a and 12b correspond to FIGS. 11a and 11b, discussed above.

Identification of Altered Substrate Properties

Figure 13B:
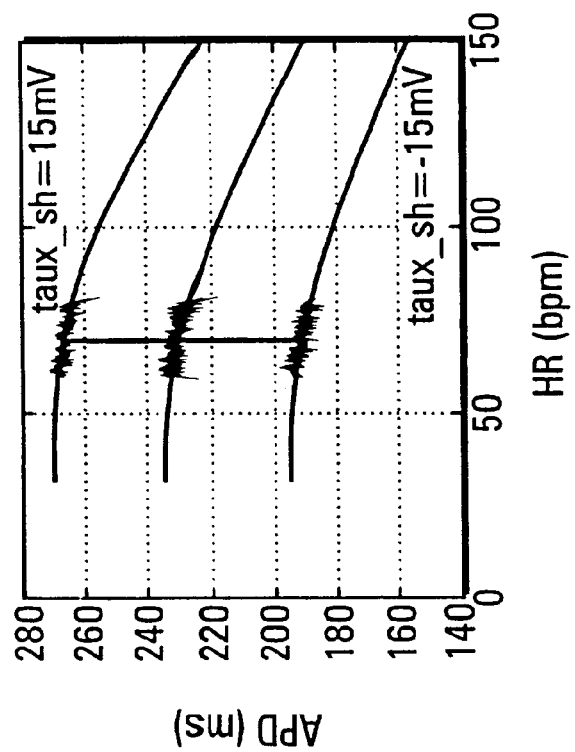
FIG. 13b is a graphical depiction of an APD and HR simulation according to the present invention.
Figure 13A:
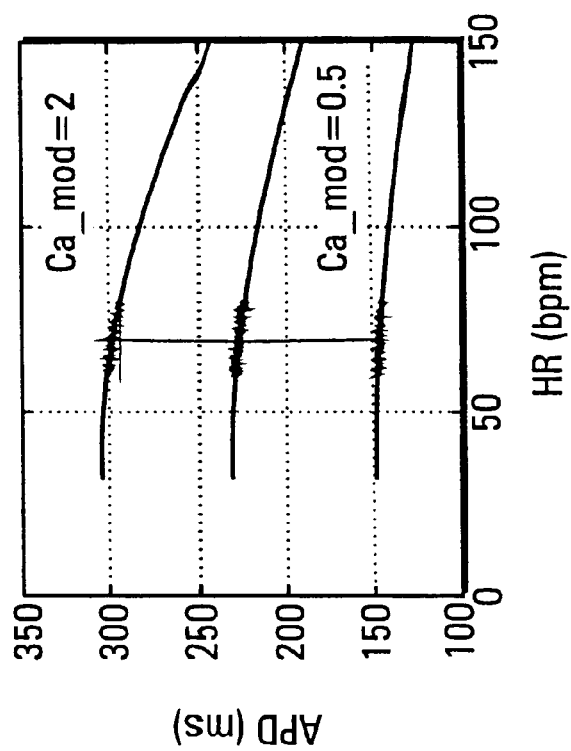
FIG. 13a is a graphical depiction of an APD and HR simulation according to the present invention.

On the basis of expectations, the process developed should be in a position to detect changes in the substrate properties. That capability was tested using the physiological cell model in which the permeability of the Ca-channel was modified and/or the relaxation curve $\tau_x(V_m)$ of the dynamic K-channel was displaced along the abscissa. Table 1, below summarizes the values which describe both the changes at the ion channels and reproduce the system parameters ($\tau_x$, g) determined from the simulated measurements. These results are also shown in graph form in FIGS. 13a and 13b.

Table 1 shows parameter values which were calculated back for modified cell behavior, wherein Ca__mod multiplicatively varies the permeability of the Ca-channel and $\tau_x$ represents the displacement of the relaxation curve of the dynamic channel.

TABLE 1

| | | Parameter Values | | | |
| --- | --- | --- | --- | --- | --- |
| | Reference | Values for altered cell properties | | | |
| Parameter | value | Ca__mod = 0.5 | Ca__mod = 2 | taux__sh = −15 V | taux__sh = 15 V |
| $\tau_x$ (mV) | 165.8369 | 173.0361 | 163.9346 | 190.1786 | 158.9006 |
| g | 1.0 | 0.5608 | 1.3717 | 0.6885 | 1.2401 |

It will be seen from Table 1 that, upon an increase in the level of permeability of the Ca-channel (Ca__mod>1), on the basis of the relationships defined by Equations (11a,b) and (18b), as expected, the value of g also rises. If we consider the relaxation curve $\tau_x(V_m)$, it is also to be noted that, in conformity with Table 1, the values of $\tau_x$ rise in the event of a displacement towards the left and become smaller in the event of displacement towards the right.

It is noted that the modifications caused on the physiological cell model do not act solely on only one reverse-calculated system parameter or the other, but they to a certain degree depend on each other. This dependence can be attributed to both the simplifications involved in consideration of the model and because g (by virtue of the relationship defined by Equations (11a,b)) depends on the relationships of the Ca- and K-current amplitudes and not on the conductivity levels themselves. A displacement of the relaxation curve of the dynamic K-channel acts primarily on the K-current itself, but also indirectly (by way of the transmembrane voltage which is altered thereby) on the Ca-current. It will thus be understood that the displacement of the relaxation curve also acts on g.

The other relationship can be justified in similar terms. If the permeability of the Ca-channel is modified (by way of Ca_mod), that also entails changes in the action potential form, which in turn influences the relaxation behavior of the dynamic K-channel. In the parameter reverse calculation that fact results in a correspondingly different value of $\tau_x$.

Figure 14B:
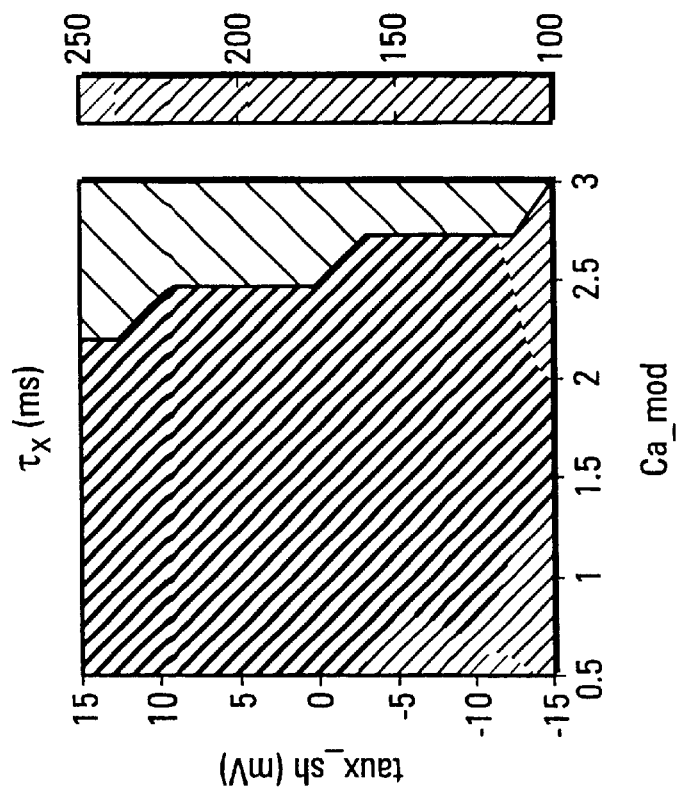
FIG. 14b is a graphical depiction of cellular model parameters according to the present invention.
Figure 14A:
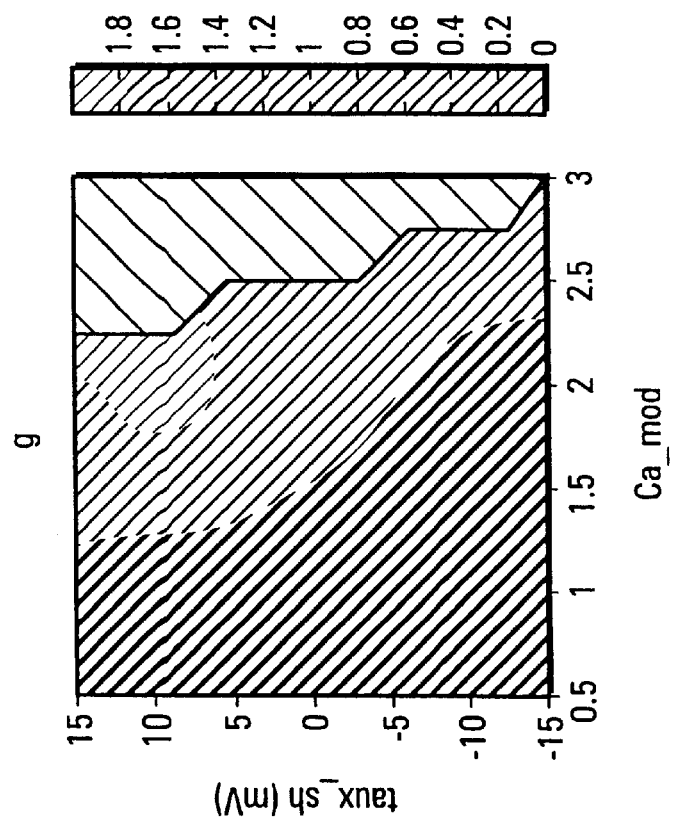
FIG. 14a is a graphical depiction of cellular model parameters according to the present invention.

The coupling of the identified system parameters ($\tau_x$, g) can be particularly clearly seen from FIGS. 14a and 14b as the contour height lines do not extend parallel to any one of the two parameter axes. These graphs represent the relationship to the system parameters $\tau_x$ and g, which is involved in the range of variations in the cellular model parameters Ca_mod and taux_sh. The limits of the ranges, within which the parameters of the physiological cell model were varied, can be read out of FIGS. 14a and 14b. The grid pattern amounted in each case to 11 subdivisions per parameter range. In that respect 100 stimulation cycles were considered (for each grid point) for parameter estimation.

For parameter values (Ca_mod and taux_sh), within the areas shown by hatching in FIGS. 14a and 14b, the cell model behaves pathologically, i.e., EADs occur. In this extreme case the model considerations are no longer applicable. In addition, for deriving the mathematical relationship between APD and HR. the application of the process developed therefrom for parameter estimation purposes is also unallowable in this region. Therefore, no values for $\tau_x$ and g can be specified in the hatched area. However, it is striking that the steepest gradient of g in FIG. 14a points precisely in the direction of that danger zone.

Use of the Method for the Prediction of EAD-based Arrhythmia Phenomena

When rigorously applied, the method which follows from the previous section results in the development of a diagnosis tool which may be used both for early detection and also for observing the progress of cellular diseases. Although it will be understood that there are many uses for the identification process presented herein, reference will only be made here by way of example to the clinical option of using the method of this invention as an EAD-predictor.

The mechanisms and cellular causes of arrhythmogenesis are multi-level and complex, and altered substrate properties can trigger a tachycardia in the most widely varying ways. For example, the relationship between the occurrence of EADs and the reentry-based arrhythmia form "Torsade de Pointes" has been clinically demonstrated. However, these mechanisms have also been explained and reproduced in other model studies. Accordingly, it should be understood that the process according to this invention can also be used for the early detection of tachycardia.

It also possible to determine why a substrate is or is not predestined for an arrhythmia. In strict terms, it is only possible to talk of prediction insofar as it is possible to extrapolate into the future from observing trends in the past. The process of the current invention itself, however, only supplies information relating to the instantaneous actual state. Based on these considerations, an exemplary embodiment of the predictor system according to this invention for EAD-governed tachycardia phenomena is set forth in the following simulation.

Figure 15B:
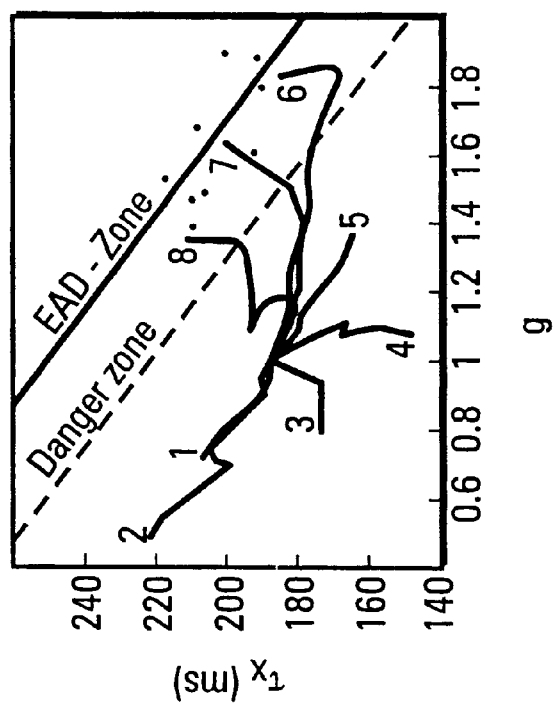
FIG. 15b is a graphical depiction of a predictor simulation for EAD-governed tachycardia according to the present invention.
Figure 15A:
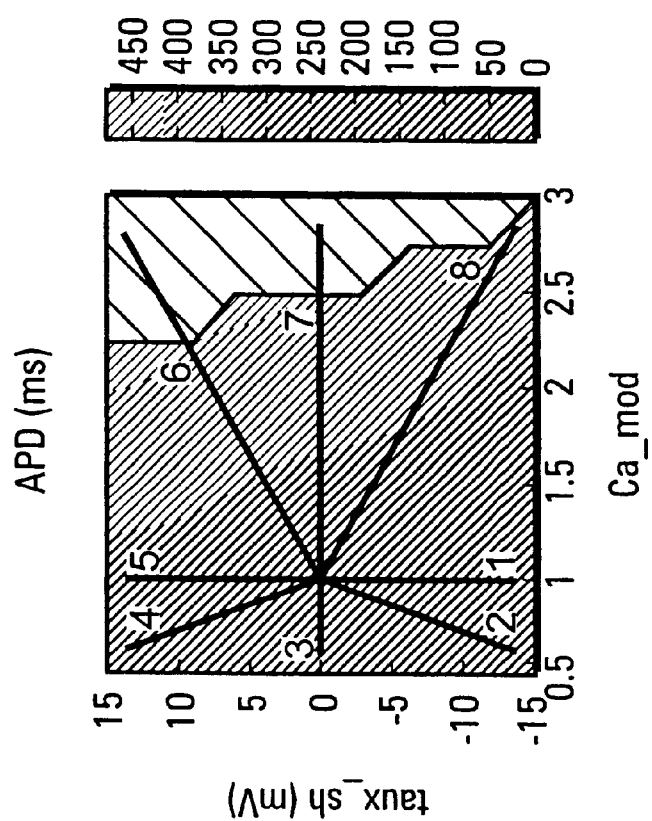
FIG. 15a is a graphical depiction of a predictor simulation for EAD-governed tachycardia according to the present invention.
Figure 16:
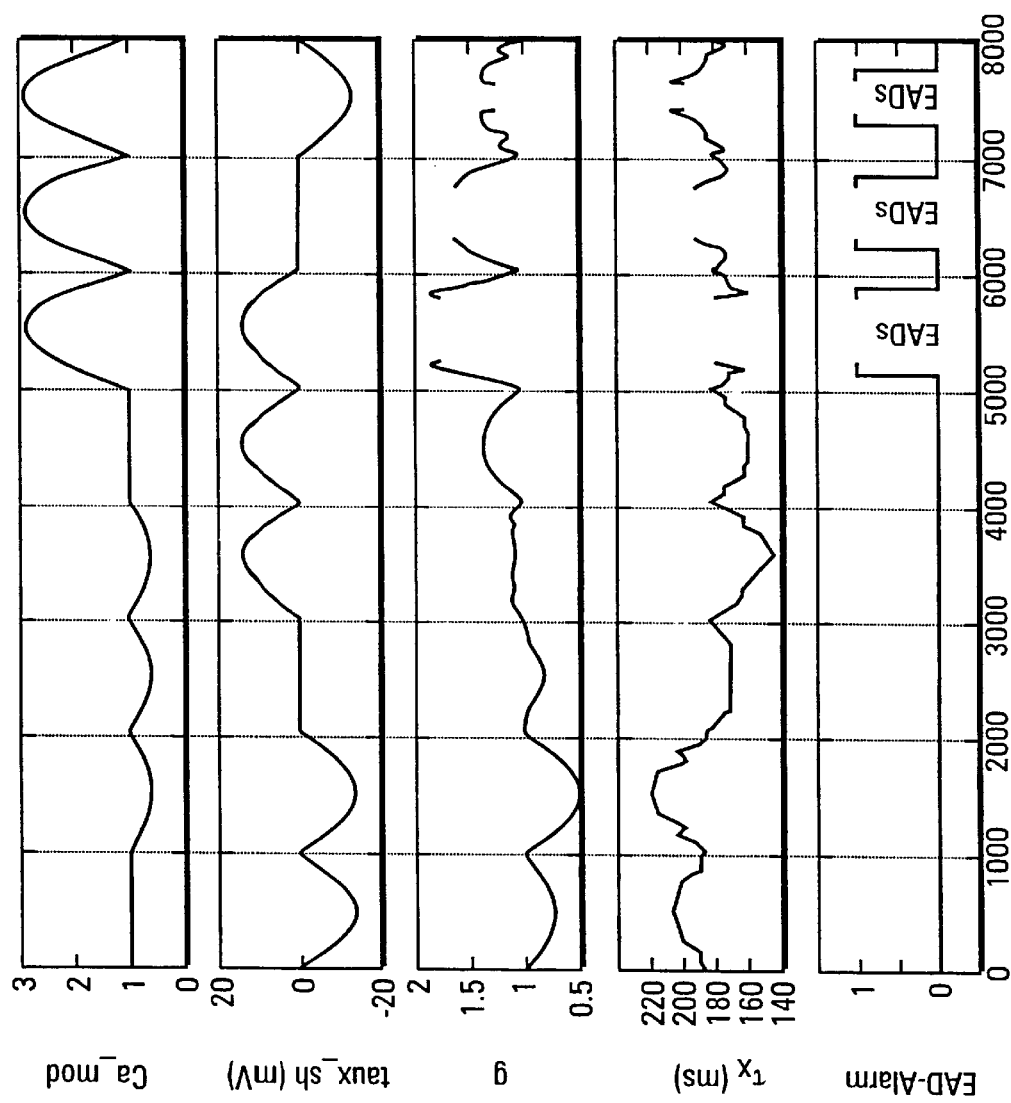
FIG. 16 is a graphical depiction of a time-elapsed predictor simulation for EAD-governed tachycardia according to the present invention.

FIG. 15a shows the range of variations in the cellular parameters which can cause changes in substrate properties. The functional value illustrated is the corresponding action potential duration. Shown superimposed on the image are radiating trajectories (the origin corresponds to the healthy normal state of the substrate), along which the substrate properties change, in the model calculation. FIG. 16 shows in the top two charts how the changes to the substrate properties vary over time. FIG. 15b shows the image of those trajectories in the parameter space ($\tau_x$, g). The limit points of the hatched EAD-region were transformed from FIG. 15a into that parameter space and a regression straight line was passed through those points. In the parameter space, these regression lines represent the limit in relation to the EAD-zone. At a (freely definable) safety spacing a further straight line is set parallel thereto, which marks the danger zone. If the working point ($\tau_x$, g) moves beyond that limit, the algorithm sets an alarm flag.

FIGS. 17a and 17b afford a more detailed view of the process of the invention. Two examples illustrate how the process detects and signals danger about 100 heart beats before the occurrence of EADs. It will be noted that the precise number of heart beats depends in specific terms on the speed at which the substrate properties change. However, it is to be assumed that a diseased condition does not suddenly occur from one heart beat to the other, but rather involves a gradual progression. On the basis of this expectation, there should be a sufficient period of time available for therapeutic measures.

As can be seen by reference to the two examples in FIGS. 17a and 17b, the process reacts not only to an EAD-danger, but is also capable of assessing at an early stage in a differentiated fashion the extent of the EADs. While in the upper example EADs occur only sporadically, the lower example, by virtue of multiple EADs, involves a serious prolongation of the action potential duration. The Figures also illustrate that at the peaks in the course of these EADs a new excitation comes into the refractory period, i.e., there is a transient excitation block. As already shown in the literature, in the case of a transient excitation block the occurrence of a revolving excitation is much more probable than in a non-transient excitation.

Although at the time that danger is signaled by the process no variation is visible at the action potentials (FIGS. 17a and 17b, left-hand charts), based on the identified system parameters the process according to the present invention is already capable of establishing what the EADs will look like. Indications with respect to EADs are also supplied by the parameter g alone, the gradient of which is at its steepest in the direction of the danger zone (as shown in FIGS. 14a and 14b). The EAD-forms to be expected, however, can only be more accurately specified with the assistance of the parameter $\tau_x$.

As already shown in the literature, the fact that the action potential duration drastically increases is a necessary criterion in determining the occurrence of EADs. This fact is also confirmed by the simulations summarized in FIGS. 15a and 15b. However, it is not possible to simply define an APD-threshold value as an adequate criterion as that threshold value varies by about 100 ms along the EAD-limit shown in FIG. 15a. Therefore, the specificity of the process developed here is superior in determining the risk of arrhythmia compared to that of a simple APD-criterion Summary On the basis of the mathematical description of a physiologically justified cell model according to the present invention, it is possible by virtue of simplifying approaches to afford the basis for a theoretical system identification for the early detection of cardiac disrhythmia. The focal point of the considerations in such early detection is the dynamic relationship between heart rate and repolarization time, the correspondence of which to arrhythmogenesis has been investigated and confirmed by numerous experimental studies in the literature.

The outcome of system identification results in calculation rules which make it possible to calculate back to the amplitude relationship of the Ca- and K-currents and to determine the time constant of the dynamic K-channel. This calculation involves parameters which provide a direct relationship to clinical findings and makes it possible to assess the risk of arrhythmia on the basis of physiological criteria. Accordingly, the input signals required for system analysis, are limited to the heart rate and the repolarization time which can be ascertained from common intracardial measurement signals (for example IEGM).

For the purposes of a numerical calculation of the defined system parameters, implementation provisions for an algorithm were also worked out. This algorithm optimizes the level of reliability and accuracy at a nonetheless viable calculation involvement. As in additional advantage, the deflection of the system required for system observation purposes does not have to be imposed from the exterior and thus there is no fear of non-physiological intervention in the excitation procedure. The simulation results show that informative results can be achieved even at natural heart-rates (with variations in the range of 60–80 bpm). This means that, playing the part of a diagnostic observer, in an energy-saving manner, the implant according to the present invention can monitor the functionality of the syncytium and initiate therapeutic measures only when required. Finally, it can be concluded that this process not only provides a binary answer to the question of arrhythmia endangerment, but also affords information as to how serious are the consequences of the altered substrate properties.

What is claimed is:

1. A cardioelectric system for early detection of a tachycardia of a heart, comprising:

measurement means for measuring the heart rate and the action potential duration, the measurement means having at least one output for the output of at least two pairs of measurement values for the heart rate and the action potential duration;

measurement value processing means connected to the at least one output of the measurement means for receiving the measurement values and deriving time-variant parameters which characterize the time dependent permeabilities of the calcium channel, the static potassium channel, and the dynamic potassium channel of the heart muscle cells;

memory means for storing a plurality of comparative time-variant parameters characterizing a tachycardia risk range; and an evaluation unit connected to the measurement value processing means for receiving at least one pair of the time-variant parameters, and to the memory for receiving the comparative time-variant parameters, and for comparing the at least one pair of the time-variant parameters to the comparative time-variant parameters and outputting a tachycardia risk signal if the comparison of the at least one pair of the time-variant parameters with the comparative time-variant parameters indicates that the at least one pair of the time-variant parameters is within the tachycardia risk range.

2. The cardioelectric system as set forth in claim 1 wherein the system is adapted to measure at least two measurement values at two different measurement times, wherein the system further comprises:

second memory means connected to the measurement value processing means for storing the time-variant parameters derived from the two most recent measurement times;

and trend-determining means connected to the second memory means for determining a trend for the future development of the time-variant parameters on the basis of the stored time-variant parameters, wherein the evaluation unit is connected to the trend-determining means and outputs the tachycardia risk signal when the time-variant parameters are in the proximity of the tachycardia risk range and the trend for future development of the time-variant parameters indicates that the time-variant parameters are approaching nearer to the tachycardia risk range.

3. A cardioelectric system as set forth in claim 1 wherein the apparatus is adapted to measure at least two measurement values at two different measurement times, wherein the system further comprises:

second memory means connected to the measurement value processing means for storing the time-variant parameters derived from the two most recent measurement times;

and trend-determining means connected to the second memory means for extrapolating future time-variant parameters from the stored time-variant parameters, wherein the evaluation unit is connected to the trend-determining means for comparing the extrapolated future time-variant parameters to the comparative values stored in the memory means and to output the tachycardia risk signal if the comparison of the extrapolated future time-variant parameters with the comparative values indicates that the extrapolated future time-variant parameters lie within the tachycardia risk range.

4. A cardioelectric system as set forth in one of claims 1 through 3 wherein a first of the time-variant parameters derived by the measurement value processing means is a time constant of the dynamic potassium ion current, and a second of the time-variant parameters (g) derived by the measurement value processing means is a function of the amplitude of the dynamic potassium ion current ($A_{Kx}$) and the amplitudes of the calcium ion current ($A_{Ca}$) and the static potassium ion current ($A_{K1}$) in accordance with the equation:

$$g=((A_{Ca}-A_{K1})/A_{Kx}).$$

5. A cardioelectric system as set forth in claim 1 further comprising an electrostimulator wherein the electrostimulator is connected to the evaluation unit for receiving the tachycardia risk signal and delivering at least one tachycardia-combating electrical stimulation pulse to the heart in response to the tachycardia risk signal.

6. A cardioelectric system as set forth in claim 5 wherein the electrostimulator is either a cardioverter or a defibrillator.

7. A Cardioelectric system for early detection of a tachycardia of a heart, comprising:

measurement means for measuring the heart rate ($L_m$) and the action potential duration ($T_m$), the measurement means having at least one output for the output of at least two pairs of measurement values for the heart rate and the action potential duration;

measurement value processing means connected to the at least one output of the measurement means for receiving the measurement values and deriving time-variant parameters ($\tau_x$ and g) in accordance with the following basis equation:

$$T(L, \tau_x, g) \approx T_0(L) + \left.\frac{\partial T}{\partial \tau_x}\right|_{\tau_{x0}, g_n} \cdot (\tau_x - \tau_{x0}) + \left.\frac{\partial T}{\partial g}\right|_{\tau_{x0}, g_0} \cdot (g - g_0)$$

wherein T is the depolarization time, L is the cycle length, $\tau_x$ is a time constant of dynamic potassium ion current, g is the ratio between the permeabilities of a calcium ion channel ($A_{Ca}$) and a static potassium channel ($A_{K1}$), and a dynamic potassium channel ($A_{kx}$) of the heart muscle cells and the index 0 indicates initial values, and based on the basis equation, and at least two pairs of measurement values ($L_m$, $T_m$) the time-variant parameters are found according to the following parameter extraction equation:

$$u_{0,m}\tau_{0,m} + v_{0,m}g = w_{0,m},$$

where:

$$u_{0,m} = \left.\frac{\partial T}{\partial \tau_x}\right|_{\tau_{x0}, g_0} = u_0(L_m),$$

$$v_{0,m} = \left.\frac{\partial T}{\partial g}\right|_{\tau_{x0}, g_0} = v_0(L_m),$$

$$w_{0,m} = w_0(L_m) = T_m - T_o(L_m) + u_0(L_m)\tau_{x0} + v_0(L_m)g_0,$$

m=1 . . . M, and

M≧2;

memory means for storing a plurality of comparative time-variant parameters characterizing a tachycardia risk range; and an evaluation unit connected to the measurement value processing means for receiving at least one pair of the time-variant parameters, and to the memory means for receiving the comparative time-variant parameters, and for comparing the at least one pair of the time-variant parameters to the comparative time-variant parameters and outputting a tachycardia risk signal if the comparison of the at least one pair of the time-variant parameters with the comparative time-variant parameters indicates that the at least one pair of the time-variant parameters is within the tachycardia risk range.

* * * * *